United States Patent [19]
Huang et al.

[11] Patent Number: 5,147,347
[45] Date of Patent: Sep. 15, 1992

[54] DISPOSABLE GARMENT HAVING A REFASTENABLE ADHESIVE TAPING SYSTEM

[75] Inventors: Yung-Hsiang Huang, Appleton; Dave A. Soerens, Neenah; Ruth A. Lachapell, Menasha; Paul M. Linker, III, Appleton, all of Wis.

[73] Assignee: Kimberly-Clark Corporation, Neenah, Wis.

[21] Appl. No.: 642,612

[22] Filed: Jan. 17, 1991

[51] Int. Cl.$^5$ .............................................. A61F 13/15
[52] U.S. Cl. ..................................... 604/390; 604/389
[58] Field of Search ............ 604/389, 390, 391, 385.1, 604/358

[56] References Cited

U.S. PATENT DOCUMENTS

| | | | |
|---|---|---|---|
| 3,867,940 | 2/1975 | Mesek et al. | 128/287 |
| 4,210,144 | 7/1980 | Sarge, III et al. | 128/287 |
| 4,296,750 | 10/1981 | Woon et al. | 128/287 |
| 4,643,730 | 2/1987 | Chen et al. | 604/390 |
| 4,655,761 | 4/1987 | Grube et al. | 604/389 |
| 4,710,190 | 12/1987 | Wood et al. | 604/389 |
| 4,753,649 | 6/1988 | Pazdernik | 604/389 |
| 4,769,024 | 9/1988 | Pike et al. | 604/390 |

FOREIGN PATENT DOCUMENTS

| | | |
|---|---|---|
| 0148587A2 | 7/1985 | European Pat. Off. |
| 0306232 | 3/1989 | European Pat. Off. ............ 604/389 |
| 2129689A | 5/1984 | United Kingdom . |
| 2135568A | 9/1984 | United Kingdom . |

Primary Examiner—Randall L. Green
Assistant Examiner—R. Clarke
Attorney, Agent, or Firm—Paul Yee

[57] ABSTRACT

An article includes a distinctive refastenable adhesive taping system. The article comprises an outer cover which has waistband sections positioned at opposite ends thereof and has an intermediate section which interconnects the waistband sections. The outer cover includes a securing zone which is located at a first of the waistband sections and which provides a landing surface appointed for receiving adhesion of one or more adhesive tabs thereon. The securing zone has a selected peak tensile strength and a selected rigidity value. An adhesive tab is located at at least one lateral side edge of a second of the waistband sections for securing the waistband sections around a wearer. The tab includes a backing layer and an adhesive layer, and, when adhered to the landing surface, has a 180° peel adhesion value which is less than the peak strength of the securing zone. The backing layer has a rigidity value selected to provide a rigidity ratio of not more than about 10:1, where the rigidity ratio is determined by dividing the backing layer rigidity value by the securing zone rigidity value. The securing zone and adhesive tab thereby provide an improved refastenable taping system.

70 Claims, 10 Drawing Sheets

DISPOSABLE GARMENT HAVING A REFASTENABLE ADHESIVE TAPING SYSTEM

TECHNICAL FIELD

The present invention pertains to articles which employ adhesive tape tab fastening systems for securement of the article about the body of a wearer. More particularly, the present invention relates to absorbent garment articles employing pressure-sensitive adhesive tape tabs which can be fastened, released and refastened a plurality of times onto a target adhesion region of the article.

BACKGROUND OF THE INVENTION

Articles, such as disposable garments, have employed adhesive tape tabs to secure the garment onto the body of a wearer. For example, absorbent personal care garments have employed adhesive tabs to secure the waistband portions of the garment about the wearer's waist.

Although a disposable garment, such as a gown, diaper or incontinence garment, is intended for limited use and is not intended to be laundered or cleaned for reuse, it has been desirable to employ a refastenable tape tab system in which the tape tab can be fastened and then peeled away and readhered several times to an appointed tape attachment zone. Ordinarily, the fastening system has employed a relatively large level of adhesion between the adhesive tab and the tape attachment zone to assure a secure fastening. The adhesion force must be sufficient to prevent premature release and opening when the infant moves about. The level of adhesion force has typically been greater than the load capacity of that section of the garment outer layer to which the fastening tab is adhered. As a result, it has been difficult to peel the adhesive tab away from the garment without tearing or excessively stretching the outer layer. Various techniques have been employed to reinforce selected securing zone regions against which the adhesive tape tab can be repeatedly adhered, removed, and readhered.

Some conventional techniques have employed a separate layer of polymer sheet material bonded to the outer cover sheet of a disposable diaper. For example, see U.K. Patent Application GB 2 129 89 A published May 23, 1984, with L. Widlund as inventor; European Patent Application EP 0 080 647 A1 published Jun. 8, 1983, with R. De Jonckheere, et al. as inventors; and U.K. Patent Application GB 2 135 568 A published Sep. 5, 1984, with J. Pasinato, et al. as inventors.

Other diaper structures have reinforced the backsheet material with a structural material, such as scrim or adhesive, to prevent stretching and rupture of the backsheet due to tension imparted by fastening tape tabs during diapering, wearing of the diaper and removal of the diaper from an infant. For example, see U.S. Pat. No. 3,867,940 issued Feb. 25, 1975, to F. Mesek, et al.

Garment structures have also employed a refastenable tape system in which the outer cover of the garment is reinforced with a pattern of adhesive. For example, U.S. Pat. No. 4,210,144 issued Jul. 1, 1980, to H. Sarge III, et al. reinforces the backsheet by coating it with a material having a high tensile strength and a low elongation tensile force property relative to the backsheet material. U.S. Pat. No. 4,296,950 issued Oct. 27, 1981, to L. S. Woon, et al. reinforces the backsheet of a garment with a layer of hot melt adhesive to provide strengthened tape securement zones. The hot melt adhesive layer has a lower modulus of elasticity than the film and is applied in a heat-softened condition.

Refastenable tape systems have employed multi-piece tapes which include a fastening tape portion and a target tape portion. Once the target tape portion has been initially positioned and secured onto a selected portion of a garment, the fastening tape can then be repeatedly removed and readhered. For example, see European Patent Application EP 0 148 587 A2 published Jul. 17, 1985, with P. Pape as inventor.

Adhesive taping systems have also employed specially tailored adhesives. For example, U.S. Pat. No. 4,769,024 issued Sep. 6, 1988 to Charles O. Pike et al. (Century Adhesives Corporation) describes a system which employs less aggressive adhesives to prevent the tearing of the outer cover of a garment.

Conventional refastenable tape systems, such as those described above, have not been completely satisfactory. For example, multi-piece tape systems, such as those described in EP 0 148 587 A2, can require a precise balance between the adhesive force which secures the target tape member to the outer surface of the garment and the adhesive force which secures the fastening tape tab onto the target member. If the adhesive force between the fastening tape and the target member is too high, the target member may be pulled or torn away from the garment. Also, the target member is relatively small and allows only a small amount of repositioning of the fastening tape tab once the target member is affixed onto the outer surface of the garment. Systems which employ separate sheet layers of plastic film or scrim material bonded to the garment outer cover can require complicated and costly manufacturing equipment and processes. Conventional systems which employ layers or patterns of hot melt adhesive applied to the garment outer cover can excessively stiffen the surface of the garment and degrade the aesthetic appeal, and systems which employ reduced levels of adhesion between the adhesive tabs and the tape attachment zone have been susceptible to premature release.

BRIEF DESCRIPTION OF THE INVENTION

Generally stated, the present invention provides a distinctive article comprising an outer cover layer having waistband sections positioned at opposite ends thereof, and having an intermediate section which interconnects the waistband sections. The outer cover includes a securing zone which is located at a first of said waistband sections and which provides a landing surface appointed for receiving adhesion of one or more adhesive tabs thereon. The securing zone has a selected peak strength and a selected rigidity value. An adhesive tab is located at at least one lateral side edge of a second of said waistband sections for securing the waistband sections around a wearer. The tab includes a backing layer and an adhesive layer. When adhered to the landing surface, the tab has a 180° peel adhesion value which is less than the peak strength of the securing zone. The backing layer has a rigidity value selected to provide a rigidity ratio of not more than about 10:1, where the rigidity ratio is determined by dividing the backing layer rigidity value by the securing zone rigidity value. The securing zone and adhesive tabs thereby provide a refastenable taping system.

The article of the invention can advantageously provide a distinctive combination of easy refastenability and improved resistance to premature, unintended release of the adhesive tab from the appointed securing zone. The adhesive tab can be readily peeled away from the securing zone without causing excessive stretching or tearing of the outer cover layer. In addition, the appropriate matching of the rigidity of the tape backing layer to the rigidity of the securing zone can also allow the tape backing layer to flex in approximate synchronization with the flexing of the outer cover layer caused by motions of the wearer. The refastenable taping system can be configured to provide easy removal of the adhesive tab from the securing zone upon the application of relatively low levels of peeling force while still providing adequate resistance to premature pop-opening of the fastening system.

BRIEF DESCRIPTION OF THE DRAWINGS

The present invention will be more fully understood and further advantages will become apparent when reference is made to the following detailed description of the invention and the drawings in which:

FIG. 9A representatively shows a side view of the test specimen illustrated in FIG. 9;

DETAILED DESCRIPTION OF THE INVENTION

The following detailed description of the invention will be made in the context of a disposable absorbent garment article, such as a disposable diaper. It will, however, be readily apparent to a person having ordinary skill in the art, that the structures of the present invention may also be employed with other articles such as gowns, aprons, feminine care articles, incontinence garments, and the like.

Figure 1:
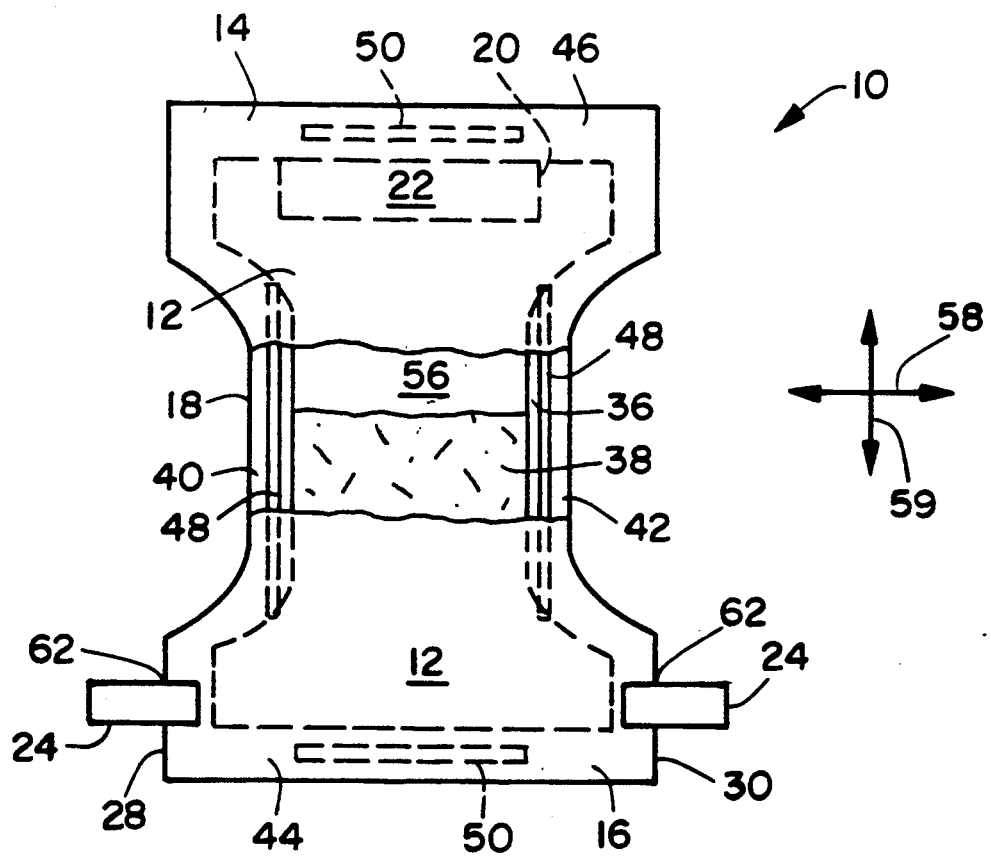
FIG. 1 representatively shows a plan view of a disposable diaper article having a refastenable tape system.

With reference to FIG. 1, a representative article of the invention, such as diaper 10, comprises a flexible outer layer, such as outer cover layer 12. The outer cover has waistband sections 14 and 16 positioned at opposite ends of the outer cover, and has an intermediate section 18 which interconnects the waistband sections. The outer cover includes a securing zone substrate 20 which is located over at least a portion of a first of the waistband sections, such as front waistband 14. The securing zone is generally defined by the area within the dotted lines, and provides a landing surface 22 appointed for receiving adhesion of one or more adhesive tabs 24 thereon. Securing zone 20 has a selected peak strength and a selected rigidity value. An adhesive tab 24 is suitably located and attached at at least one lateral side edge 28, 30 of a second of said waistband sections, such as rear waistband section 16, for securing the waistband sections around a wearer. Each adhesive tab 24 includes a backing layer 32 and an adhesive layer 34. When adhered to landing surface 22, the adhesive tab has a 180° peel adhesion value which is less than the peak strength of securing zone 20. Backing layer 32 has a rigidity value selected to provide a rigidity ratio of not more than about 10:1, where the rigidity ratio is determined by dividing the backing layer rigidity value by the securing zone rigidity value. The securing zone and adhesive tab thereby provide a refastenable taping system.

FIG. 1 representatively shows a plan view of diaper 10 in its flat-out, uncontracted state (i.e., with all elastic induced gathering and contraction removed) with portions of the structure being partially cut away to more clearly show the construction of the diaper 10, and with the outer, exterior surface of the diaper 10 facing the viewer. The illustrated diaper 10 has a front waistband region 12, a back waistband region 14, an intermediate crotch region 18, and a periphery which is defined by the outer margins of the diaper in which the longitudinal margins are designated 40 and 42, and the end margins are designated 44 and 46. The diaper additionally has a transverse width direction 58 and a longitudinal length direction 59.

The shown configuration of diaper 10 is generally "hour-glass" shaped or I-shaped with a central, narrowed intermediate crotch section 18 and relatively wider waistband sections 14 and 16. Optionally, the garment may have some other shape which is suitable for its intended use. For example, the diaper may have a generally rectangular shape, or a T-shape with the relatively wider, cross-arm of the "T" forming either the front or rear waistband section of the diaper.

The illustrated embodiment includes at least one adhesive tab located at each lateral side edge of rear waistband section 16. In addition, diaper 10 includes a topsheet layer 36 superposed in facing relation with outer cover 12, and an absorbent body 38 located between outer cover 12 and the topsheet. Either or both of outer cover 12 and topsheet 36 may extend past the lateral side edges of absorbent body 38 to form diaper side margins 40 and 42. In addition, either or both of outer cover 12 and topsheet 36 may extend past the longitudinal end edges of absorbent body 38 to form diaper end margins 44 and 46. In the illustrated embodiment, outer cover 12 and topsheet 36 are essentially coterminous and extend past both the lateral and longitudinal edges of the absorbent body.

Each of the diaper side margins can include one or more individual leg elastic members 48 for providing resiliently gathered gasketing cuffs about the legs of the wearer. In addition, either or both of diaper end margins 44, 46 can include one or more individual waist elastic members 50 for providing elasticized waistbands about the waist of the wearer. The diaper may further include elasticized containment flaps, such as those described in U.S. Pat. No. 4,704,116 issued Nov. 3, 1987, to K. Enloe, which is hereby incorporated by reference to extent that it is consistent herewith.

The elastic members are secured to the diaper 10 in an elastically contractible condition so that under normal conditions the elastic members will operably contract the associated margins of diaper 10. The elastic members can be secured in an elastically contractible condition in at least two ways, for example, the elastic members 34 may be stretched and then secured to diaper 10 while the diaper is in an uncontracted condition. Alternatively, the diaper 10 may be contracted, for example by pleating, and the elastic members then secured and connected to the diaper 10 while the elastic members are in their relaxed or unstretched condition. Still other techniques, such as the incorporation of heat-shrink elastic material, may be used to gather the garment.

In the embodiment illustrated in FIG 1, leg elastic members 48 extend essentially the length of intermediate crotch region 18 of diaper 10. Alternatively, the leg elastics may extend the entire length of the diaper 10, or any other length suitable for providing the arrangement of elastically contractible lines desired for the particular diaper design.

The elastic members may have any of a multitude of configurations. For example, the width of the individual elastic members may be varied from 0.25 millimeters (0.01 inches) to 25 millimeters (1.0 inches) or more. The elastic members 34 may comprise a single strand of elastic material or may comprise several separated, parallel or non-parallel strands of elastic material, and the elastic members may be applied in a rectilinear or curvilinear arrangement. In addition, the elastic members may be composed of natural rubber or a synthetic rubber, such as polyurethane elastomer, DuPont Lycra ® elastomer or the like.

The various components of diaper 10 can be assembled together employing conventional techniques. For example, the components may be attached to one another employing thermal or sonic bonds, or mechanical fasteners, such as snaps or clips. Alternatively, the components can be attached with adhesives, such as hot melt pressure-sensitive adhesives. The adhesives can be applied by employing conventional techniques, such as by spraying adhesive droplets or filaments, or by employing a plurality of generally parallel lines of hot melt pressure-sensitive adhesive oriented along the length direction of the diaper. In the shown embodiment of the invention, the diaper component elements are assembled together by employing a patterned adhesive comprising a plurality of juxtaposed, looping arrays of swirled adhesive filaments which are laid down generally along the length dimension of the diaper.

Outer cover 12 may be composed of a liquid-permeable material, but typically is composed of a liquid-impermeable material, such as a polyolefin sheet composed of polyethylene, polypropylene or the like. Alternatively, outer cover 12 may comprise a nonwoven fibrous web which has been suitably treated or otherwise configured to impart a desired level of liquid impermeability. In particular embodiments of the invention, outer cover 12 may comprise a liquid-impermeable, but vapor-permeable material, such as a microporous polyolefin sheet or a microporous nonwoven fibrous web.

The shown embodiment of outer cover 12 is composed of a thin sheet of polyolefin material, such as polyethylene, having a thickness of less than about 0.005 cm. Preferably, the thickness of outer cover 12 is not less than about 0.0025 cm and is not more than about 0.0043 cm. In the shown embodiment, outer cover 12 is also embossed or otherwise textured to provide a non-glossy, matte finish. The matte finish material is soft to the touch, provides a more garment-like appearance, and produces less rattling noise when manipulated. The material of outer cover 12 typically has a tensile strength of about 10 MPa (1500 psi), and an extensibility capable of providing an elongation-at-yield of about 5 percent.

Topsheet 36 is typically composed of a liquid-permeable, substantially hydrophobic material, such as a spunbonded web composed of synthetic polymer filaments. Alternatively, topsheet 36 may comprise a meltblown web or a bonded-carded-web composed of synthetic polymer filaments. Suitable synthetic polymers include, for example, polyethylene, polypropylene, and polyesters. The topsheet has an effective pore size that readily allows the passage therethrough of liquids, such as urine and other body exudates. Optionally, the topsheet can be treated with a surfactant to impart a desired degree of wettability, or can be selectively embossed, or can be perforated with discrete slits or holes extending therethrough.

Absorbent body 38 can comprise a liquid-retaining pad composed of airlaid hydrophilic fibers, such as cellulosic fibers commonly referred to as wood pulp fluff. Conventional pads can have a density ranging from about 0.05–0.2 gm/cc, and are sufficiently flexible to readily conform to the body of the wearer. Absorbent body 38 may also comprise a coform material composed of a mixture of cellulosic fibers and synthetic polymer fibers. For example, the coform material may comprise an airlaid blend of cellulosic wood pulp fibers and meltblown polyolefin fibers, such as fibers composed of polyethylene and/or polypropylene.

The shape of the absorbent body may be I-shaped, as representatively shown in FIG. 1, or may be generally rectangular. Alternatively, the pad shape may be T-shaped or generally oval.

Absorbent body 38 may also include an effective amount of an inorganic or organic high-absorbency material to enhance the absorptive capacity of the absorbent body. For example, absorbent body 16 can include about 5–95 weight percent high-absorbency material, and ordinarily includes about 10–25 weight percent of the high-absorbency material to provide desired levels of performance. Suitable inorganic high-absorbency materials include, for example, absorbent clays and silica gels. Organic high-absorbency materials can include natural materials, such as pectin, guar gum and peat moss, as well as synthetic materials, such as synthetic hydrogel polymers. Such hydrogel polymers can include, for example, carboxymethylcellulose, alkali metal salts of polyacrylic acids, polyacrylamides, polyvinyl alcohol, ethylene maleic anhydride copolymers, polyvinyl ethers, hydroxypropyl cellulose, polyvinyl morpholinone, polymers and copolymers of vinyl sulfonic acid, polyacrylates, polyacrylamides, polyvinyl pyridine and the like. Other suitable polymers may include hydrolyzed acrylonitrile grafted starch, acrylic acid grafted starch, and isobutylene maleic anhydride copolymers, and mixtures thereof. The hydrogel polymers are preferably lightly cross-linked to render the materials substantially water insoluble. Cross-linking may, for example, be by irradiation or by covalent, ionic, Van der Waals, or hydrogen bonding. Suitable materials are available from various commercial vendors, such as Dow Chemical Company, Hoechst-Cellanese Corporation, Allied-Colloid, and Stockhausen. Typically, the high-absorbency material is capable of absorbing at least about 15 times its weight in water, and preferably is capable of absorbing at least about 25-50 times its weight in water.

The high-absorbency material can be distributed or otherwise incorporated into absorbent body 38 employing various techniques. For example, the high-absorbency material can be substantially uniformly distributed in the fibers comprising the absorbent body. The material can also be non-uniformly distributed within the fibers to form a generally continuous gradient with either an increasing or decreasing concentration of high-absorbency material through the thickness of the absorbent body. The increasing or decreasing nature of the concentration gradient is determined by observing the concentration moving from the body side of absorbent body 38 to the outer side of the absorbent body. In an alternative arrangement, the high-absorbency material can comprise a discrete layer separate from the fibrous material of absorbent body 38, or comprise a discrete layer integral with the fibrous material of the absorbent body.

Absorbent body 38 can further include a wrap sheet 56 to help maintain the integrity of the airlaid fibrous structure and any superabsorbent particles contained therein. At least the portion of wrap sheet 56 which is positioned on the body side surface of absorbent body 38 is liquid permeable. The wrap sheet typically comprises a cellulosic material, such as a creped wadding or a high wet-strength tissue, and is commonly referred to as a tissue wrap. Optionally, the wrap sheet may comprise a woven or nonwoven web of synthetic polymer fibers.

Figure 2:
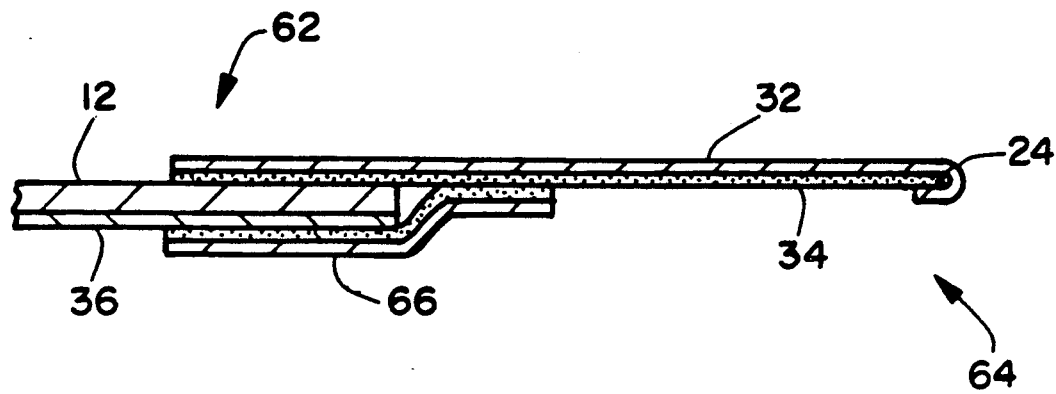
FIG. 2 representatively shows a more detailed view of a tape tab.

In diaper 10, the adhesive-type fastening system includes adhesive tape tabs 24. With reference to FIG. 2, the tape tab comprises a backing layer 32, and an adhesive layer 34 which is applied and bonded to a major surface of the backing layer. A factory bond section 62 of tab 24 is suitably attached to outer cover 12, such as by employing an adhesive bond. Alternatively, the attachment may be accomplished with thermal bonds, sonic bonds, mechanical fasteners or the like. When the tab is in a folded-over, storage position on the diaper, release layer 66 typically covers the adhesive on a user bond section 64 of the tape tab. At the appropriate time, the user separates the tab from the release layer to expose the adhesive for use in holding the diaper on an infant.

Figure 3:
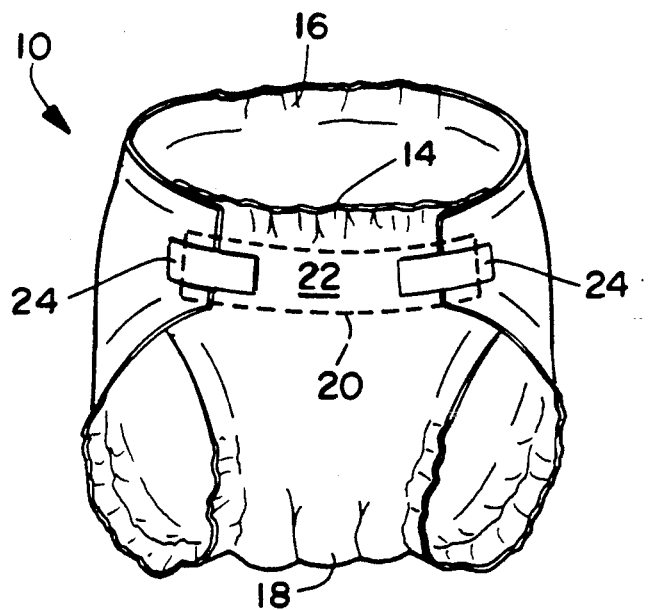
FIG. 3 representatively shows a perspective view of a diaper when worn by an infant.

When diaper 10 is worn, the waistband sections 14 and 16 of the diaper encircle the infant's waist, and intermediate section 18 extends between the infant's legs and over the infant's crotch area, as representatively shown in FIG. 3. Tape tabs 24 are then employed to interconnect the lateral side edges of back waistband portion 16 to adjacently located side sections of front waistband portion 14 and thereby secure the garment on the infant.

When the diaper is first fitted onto the infant, it has been desirable to have the capability of repositioning tabs 24 on the front waistband section of diaper 10 to provide a more secure or more comfortable fit. More particularly, it has been desirable to be able to peel tape tabs 24 from adhesive contact with outer cover 12, reposition the tape tab and adhesively refasten the tab to another select portion of outer cover 12. Thereafter during use, it has been desirable be able to check the diaper for wetness and for any other soiled condition. The user is better able to examine the diaper condition if the tape tabs can be releasably peeled from their adhesive bond with outer cover 12 to allow a further opening of the diaper for inspection. If the diaper is not soiled, it is potentially reusable, provided the diaper can be resecured about the infant. The process of peeling tape tab 24 from outer cover 12, however, can tear the backsheet material and destroys its liquid barrier function. In addition, pieces of backsheet material can remain adhered to the tape tab and render it unserviceable. The contamination produced by the residual backsheet material on the tape tab degrades the ability of the tab to refasten onto outer cover 12.

Conventional techniques for addressing these problems have included the use of a separate, extra patch of localized reinforcing material applied to either the inner surface or outer surface of outer cover 12 to strengthen the outer cover and increase its resistance to tearing in at least the reinforced patch region of the outer cover. The patch material may, for example, be a plastic strip, a scrim material, an extra layer of adhesive or the like. The patch region provides a reinforced, strengthened area which is appointed for adhesive contact with the fastening tapes and is better able to resist stretching and tearing when the adhesive tab is peeled away from the patch region. Typically, the peel adhesion value between the adhesive tab and the appointed securing zone surface is relatively high to ensure that the movements of the wearer do not cause the adhesive tabs to loosen or pop open during use. While the reinforcing patch may incorporate selected graphics or ornamental designs, the sole structural purpose of the patch has ordinarily been to provide a reinforced and/or coordinated landing surface against which the adhesive tabs may be adhered.

The addition of supplemental reinforcing mechanisms, such as the plastic strips, scrim materials or supplemental adhesive layers described above, however, can undesirably add cost and article. As a result, there has been a continued need for a refastenable adhesive taping system which does not include supplemental layers of reinforcing material which serve only to strengthen the appointed securing zone region of outer cover 12. To provide a more cost-effective design, it has been desirable to have a refastenable adhesive taping system which decreases the number of component elements in the finally assembled article. For example, it has been desirable to have a refastenable taping system wherein the securing zone region of outer cover 12 does not include an extra patch-like component, the primary purpose of which is to provide a specially prepared landing surface or a region of relatively higher strength at a selected area of the outer cover.

In particular aspects of the present invention, the refastenable taping system can provide desired levels of performance without the use of a special reinforcing patch positioned at the tape securing zone. For example, the securing zone of outer cover 12 can comprise only the outer cover material, or may comprise a composite laminate composed of the outer cover material bonded to its immediately adjacent layer of construction material, such as the wrap sheet material placed about the absorbent pad of the article. Such adjacent layer is not localized to the securing zone 20, and has a primary structural purpose other than that of reinforcing outer cover 12.

As previously mentioned, a desired refastenable taping system would meet two conditions: First, the adhesive tab should be easily peeled off the landing surface without tearing the outer cover during the unfastening-refastening process. Second, the adhesive tab and securing zone should be capable of sustaining cyclic motions without prematurely releasing or popping open when the diapers are in use. To meet the first condition, the refastenable tape system can be configured to incorporate a relatively low 180° peel adhesion value. To meet the second condition, the refastenable taping system can be configured to have a relatively high resistance to peel loads generated by peel forces applied at an angle of approximately 0° (0° peel force). Since these two conditions are somewhat contradictory, it has been difficult to predict and find the suitable combination of parameters which will produce the desired level of performance. The refastenable adhesive fastening system of the present invention, however, can advantageously provide a distinctive combination of easy peeling removal of the tape tab from its adhesion to the tape securing zone, and a high resistance to unintended pop openings.

With reference again to FIG. 1, securing zone 20 is comprises a substrate region which is located at front waistband section 14 of outer cover 12. The substrate includes a landing surface 22 which is appointed for receiving the adhesion of at least one adhesive tab 24 thereon. The illustrated embodiment is constructed such that the adhesive tabs, located at each side edge 28 and 30 of rear waistband 16, will both simultaneously attach to securing zone 20 during the intended use of diaper 10. The securing zone has a peak strength of at least about 500 gm/in (about 197 gm/cm, and preferably of at least about 700 gm/in (about 276 gm/cm). In addition, securing zone 20 can have a peak strength of not more than about 2500 gm/in (about 984 gm/cm) and preferably, of not more than about 1800 gm/in (about 709 gm/cm). As previously mentioned, the securing zone may be only a single layer of material, or may be a composite comprising two or more layers of material.

The peak tensile strength of an individual or composite material represents the maximum tensile force which a 1 inch wide strip of the material will support without breaking when the tensile force is applied perpendicular to the strip width, along the length dimension of the strip. For the purposes of the present invention, a suitable technique for determining the peak tensile strength of a material is described in the "Testing" section set forth in detail below.

Adhesive tab 24 is constructed such that, when the adhesive tab is adhered to landing surface 22 of the securing zone, the adhesive tab has a 180° peel adhesion value which is less than the peak tensile strength of securing zone 20. In further aspects of the invention, adhesive tab 24 when adhered to landing surface 22 has a 180° peel adhesion value of not more than about 67 percent of the peak strength of the securing zone substrate. Preferably, the 180° peel adhesion value is not more than about 50 percent of the peak strength of the securing zone, more preferably is not more than about 40 percent of the peak strength of the securing zone, and even more preferably, is not more than about 33 percent of the peak strength of the securing zone.

The 180° peel value represents the force which must be applied to peel apart the adhesive bond between a particular tape tab and a particular landing surface. For the purposes of the present invention, a suitable technique for determining the 180° peel value is set forth in the "Testing" section below.

To reduce the chance that the securing zone substrate could be stretched during the removal of the tape, it can be advantageous to construct the tape tab with a peel adhesion value which is about two-thirds of the peak strength of the securing zone substrate. In addition, it is important to note that during practical use conditions, the peeling angle is ordinarily between 90° and 180° when the tapes are removed by a user. Since the peel adhesion at a 90° peel angle could be as much as twice the peel adhesion which occurs at a 180° peel angle, the maximum allowable peel adhesion value should preferably be further reduced by one-half. The limitations on peel adhesion apply to both initial peel adhesion values and the values obtained after a 24 hour dwell time.

In the shown embodiment, the 180° peel adhesion value is not more than about 600 gm per inch of width (236 gm per cm of width), and preferably, not more than about 330 gm per inch of width (130 gm per cm of width).

The influence of the peeling rate on level of peel adhesion has been studied and reported in the literature. For example, see D. W. Aubrey, G. N. Welding, and T. Wong, *Journal of Applied Polymer Science.* Vol. 13, pp. 2193-2207 (1969). In general, at low speeds, the peel adhesion increases with increasing peel speed. When the peel speed reaches a certain rate, however, the peel adhesion drops as the speed is further increased. The speed at which this transition occurs (transition speed) depends primarily on the viscoelastic behavior of the adhesive. The peel adhesion at the transition speed may be kept below the strength of the securing zone substrate to avoid stretching and tearing of the substrate. In particular aspects of the invention, adhesive tab 24 is configured to provide a transition speed which is not more than about $1*10^4$ mm/minute. Preferably, the transition speed is not more than about $7*10^3$ mm/min, and more preferably, is not more than about $4*10^3$ mm/min. In other aspects of the invention, tab 24 is configured to have a transition speed which is not less than about 100 mm/minute. Preferably, the transition speed is not less than about 500 mm/min, and more preferably, is not less than about 1000 mm/min.

A qualitative determination of the transition speed can be made by conducting 180° peel adhesion tests at three speeds, such as 300 mm/minute, 1000 mm/minute, and 5000 mm/minute. If one observes a continuous increase in peel adhesion value at peel speeds between 300 and 5000 mm/minute, one could conclude that the transition speed is greater than 5000 mm/minute. If one observes a continuous drop in peel adhesion value with slip-stick behavior between 300 and 5000 mm/minute, one could conclude that the transition speed is less than 300 mm/minute. If the peel adhesion value at a peel rate of 1000 mm/minute is the largest of the three peel adhesion values, one could conclude that the transition speed occurs between 300 mm/minute and 5000 mm/minute. To more precisely determine the transition speed, one may run the peel adhesion test employing a wide range of peel speeds.

It has been found that the static shear-holding time of the adhesive bond between the tape tab and securing zone substrate does not exhibit an adequate correlation with the peel adhesion value between these components. The static shear-load can be regarded as a 0° peel test at a peel rate of approximately zero velocity. Thus, the failure mechanism is controlled by both the adhesive strength and the cohesive strength of the adhesive. It has been found that the static shear-holding time does not adequately predict or measure the performance of a tape closure system under dynamic in-use conditions.

A more appropriate technique for measuring the security of an adhesive tape fastening system is the Cyclic Test set forth in the "Testing" section below. In particular aspects of the invention, the tape tab and the landing surface of the securing zone substrate have a cyclic test value of at least about 1000 cycles. In further aspects of the invention, the taping system has a cyclic test value of at least about 1500 cycles, and preferably has a cyclic test value of at least about 2000 cycles.

Figure 4:
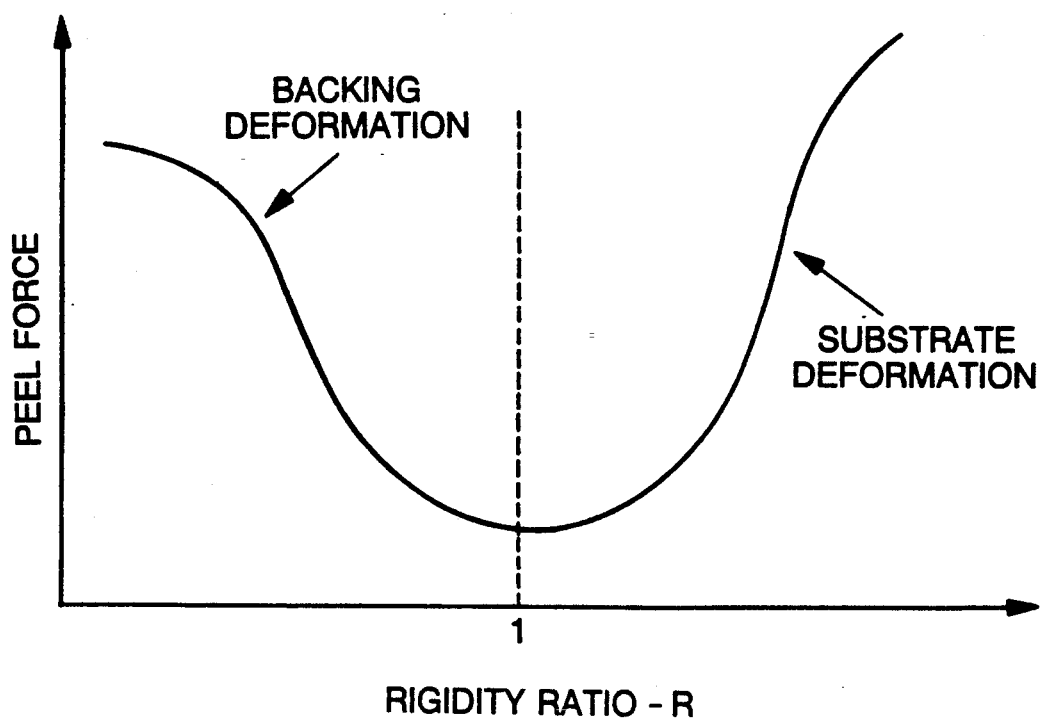
FIG. 4 schematically shows the general relationship between the peel force and the rigidity ratio for a given adhesive and backing layer thickness.

To construct a refastenable adhesive taping system having a low peel force value, it has been discovered that it is important to reduce the degree of plastic deformation of the backing and substrate as much as possible. This can advantageously be accomplished by closely matching the rigidity of the tape backing layer with the rigidity of the securing zone region of the outer cover. FIG. 4 schematically shows the general relationship between the peel force and the rigidity ratio for a given adhesive and backing layer thickness. When the rigidity ratio is less than 1, the securing zone substrate is more rigid than the tab backing layer. In this region, the effect of the plastic deformation of the tab backing layer would dominate and the degree of backing layer deformation would increase with increasing rigidity of the securing zone substrate, thereby resulting in a higher peel force. In the region where the rigidity ratio is greater than 1, the effect of the plastic deformation of the securing zone substrate would predominate, and the substrate deformation would become more severe as the rigidity of the tape backing layer is increased. It has been found that the total energy dissipation of the tape fastening system would reach a minimum when the rigidities of the tab backing layer and outer cover securing zone are closely matched. In particular, the minimum peel force would occur when the rigidity ratio is about 1.

Another parameter which can influence the peel force value is the thickness of tape backing layer 32. A first factor which can come into play is that increasing the backing layer thickness increases the rigidity value of the backing. This increases the total energy dissipation in the securing zone substrate due to the generation of more severe substrate deformation.

A second factor is that the total energy dissipation in the backing will initially increase when the backing layer thickness is small because, for a given degree of deformation, the total energy dissipation is proportional to the thickness of the backing layer. When the backing thickness is sufficiently large, however, the backing will become too stiff to undergo plastic yielding, and the total energy dissipation will begin to drop.

Figure 5:
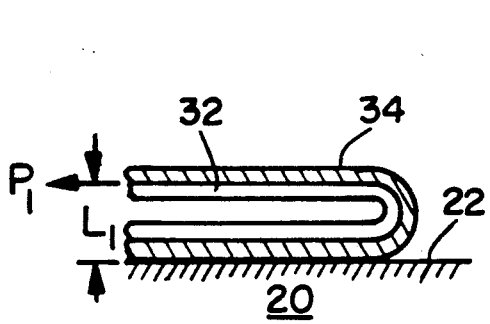
FIGS. 5 and 5A representatively show the dependence of moment arm on backing thickness, particularly an increase in moment arm due to an increase in the thickness of the tape backing layer.
Figure 5A:
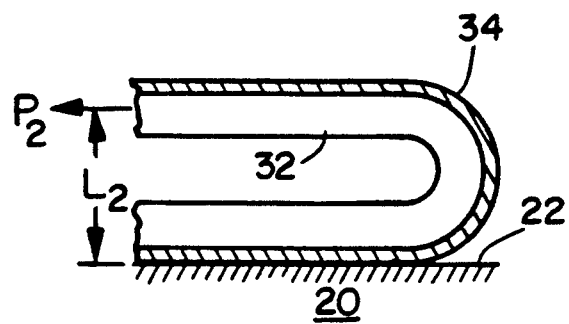

A third factor is that changing the backing layer thickness can change in the effective moment arm present when peeling the tab from the securing zone substrate. As illustrated in FIG. 5, the moment arm "L" is larger for a thicker backing layer, and the larger moment arm (leverage) means that less peel force "P" is required to remove the tape.

Figure 6:
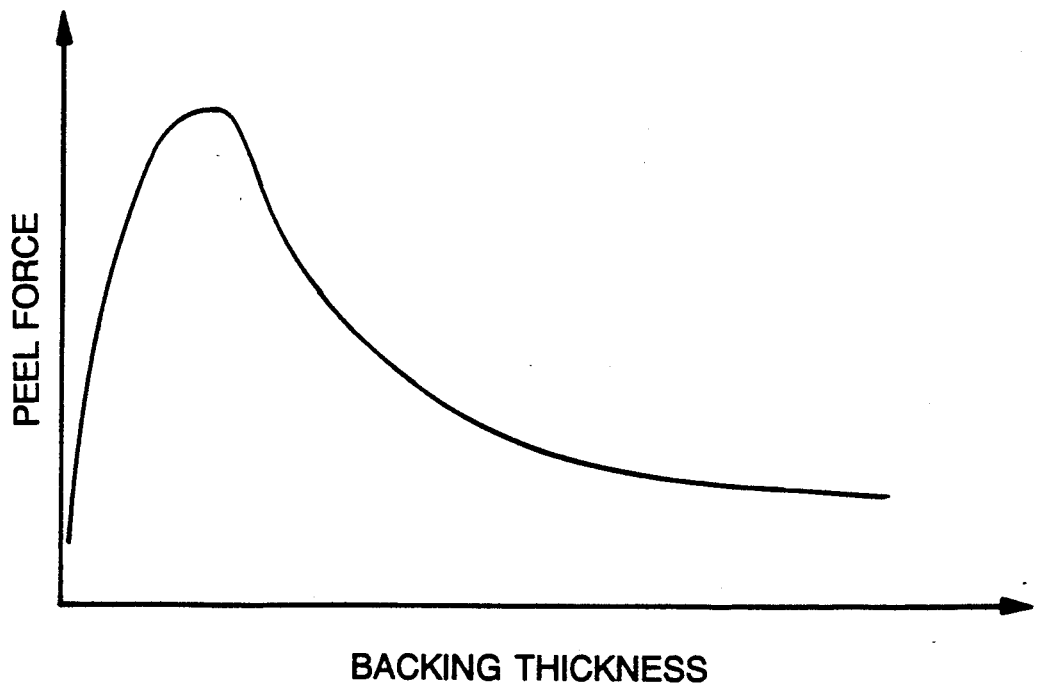
FIG. 6 schematically shows the relationship between peel force and the thickness of the tape backing layer.

In most cases, the combined contribution from the second and third factors is greater than that of the first factor. Thus, it is expected that the relationship between the peel force and the thickness of the backing layer would generally correspond to the graph illustrated in FIG. 6.

With respect to providing resistance to unintended pop opens, it is important to appreciate the dynamic debonding mechanics of the tape fastening system. When a diaper or other absorbent garment is in use, the fastening tape tabs are under periodic bending, twisting and/or stretching due to the motion of the wearer's legs and torso. Therefore, to assure the security of the adhesive joint between the tape tabs and the outer cover, the peel adhesion value cannot be too low. It has been discovered, however, that a further factor affecting the security of the tape fastening system is again the rigidity ratio between the tape tab and the securing zone region of the outer cover. The fastening system can be made more secure by incorporating relatively small rigidity ratios. With the smaller rigidity ratios, the tape tab is better able to maintain closer compliance with the various dynamic deflections of the outer cover caused by the motions of the wearer.

Thus, it has been discovered that an important parameter for providing easy peeling removal but high resistance to unintended pop-opens is the relative stiffness or rigidity ratio between the tape tab and the securing zone of the article. Accordingly, in the distinctive fastening system of the present invention, tab 24 is constructed with a backing layer 32 having a selected rigidity value. In particular, the rigidity value of backing layer 32 is not more than about 10 times the rigidity value of securing zone 20, thereby providing a rigidity ratio of not more than about 10:1. With respect to further aspects of the invention, the rigidity ratio is not more than about 7:1, and preferably, is not more than about 4:1. Other arrangements of the invention are configured with a rigidity ratio which is not less than about 1:10. Preferably, such embodiments of the invention have a rigidity ratio which is not less than about 1:7, and more preferably, have a rigidity ration which is not less than about 1:4.

In particular aspects of the invention, securing zone 20 is composed of a single or composite material having a rigidity value of not more than about $1*10^{-3}$ lb-in$^2$ per inch of width ($1.1*10^{-2}$ Newton-cm$^2$ per cm of width), and preferably, not more than about $5*10^{-4}$ lb-in$^2$ per inch of width ($5.6*10^{-3}$ N-cm$^2$ per cm of width). In addition, the securing zone may have a rigidity value of not less than about $5*10^{-7}$ lb-in$^2$ per inch of width ($5.6*10^{-6}$ N-cm$^2$ per cm of width), and preferably, not less than about $5*10^{-6}$ lb-in$^2$ per inch of width ($5.6*10^{-5}$ N-cm$^2$ per cm of width).

In other aspects of the invention, tab backing layer 32 has a rigidity value of not more than about $1*10^{-4}$ lb-in$^2$ per inch of width (1.1*10$^{-3}$ N-cm$^2$ per cm of width), and preferably, not more than about 5*10$^{-5}$ lb-in$^2$ per inch of width (5.6*10$^{-4}$ N-cm$^2$ per cm of width). In addition, the backing layer may have a rigidity value which is not less than about 5*10$^{-7}$ lb-in$^2$ per inch of width (5.6*10$^{-6}$ N-cm$^2$ per cm of width), and preferably, not less than about 5*10$^{-6}$ lb-in$^2$ per inch of width (5.6*10$^{-5}$ N-cm$^2$ per cm of width).

Once the desired rigidity value of the tab backing layer is determined, it can be advantageous to select a backing layer material which has a relatively low Young's modulus (E). For a given rigidity value, a low modulus would allow the use of a thicker backing layer, and as previously described, the greater thickness dimension could allow easier unfastening of the tape tab from its adhesion to the surface of the securing zone. Accordingly, particular aspects of the invention include a tab backing layer material having a modulus of not more than about 2*10$^4$ psi (about 1.38*10$^5$ kPa) Preferably, the backing layer modulus is not more than about 8*10$^3$ psi (about 5.52*10$^4$ kPa), and more preferably, is not more than about 3*10$^3$ psi (about 2.07*10$^4$ kPa) to provide improved performance. In addition, the tab backing layer can advantageously be configured with a thickness within the range of about 2-6 mils (about 5.1*10$^{-3}$ cm $-$1.52*10$^{-2}$ cm). Preferably, the backing layer thickness is at least about 3 mils (7.6*10$^{-3}$ cm), and more preferably, the thickness is at least about 4 mils (1.2*10$^{-2}$ cm).

With respect to the present invention, the rigidity value of a material generally represents the material's "flexural rigidity", as determined when the material is substantially dry. The flexural rigidity is the product of the Young's modulus times the area moment of inertia of a 1 inch wide sample of the material. Accordingly, for the tape backing layer, the rigidity value can be written in the form $$R_b = E_b * I_b \tag{1}$$

where:
$E_b$ = Young's modulus of the backing layer
$I_b$ = Area moment of inertia of the backing layer.

The formula for the area moment of inertia depends on the reference plane chosen for the calculation. Since the primary concern is with the relative rigidity (rigidity ratio) of the tape backing layer to the outer cover, the choice of the reference plane should be consistent for both the backing layer and outer cover. For the purposes of the following calculations, the reference plane is a middle plane midway through the thickness dimension of the sample of material.

With respect to its middle plane, the moment of inertia of the backing layer is described by $$I_b = w * h_b^3 / 12 \tag{2}$$

where:
w = width of the backing layer
$h_b$ = thickness of the backing layer

Substitution of equation (2) into equation (1) gives $$R_b = E_b * w * h_b^3 / 12 \tag{3}$$

Thus, once $E_b$ and $h_b$ are measured, the rigidity value of the backing layer per inch of width can be calculated from equation (3) by assigning, w = 1 inch.

For example, the securing zone may be a two-layer composite composed of outer cover 12 and wrap sheet 56 which are at least partially bonded together by a suitable pattern of construction adhesive. Since outer cover 12 and wrap sheet 56 may not be completely bonded together, it may be necessary to determine the rigidities in both the bonded and unbonded areas to evaluate the apparent/average rigidity value of the securing zone.

Figure 7:
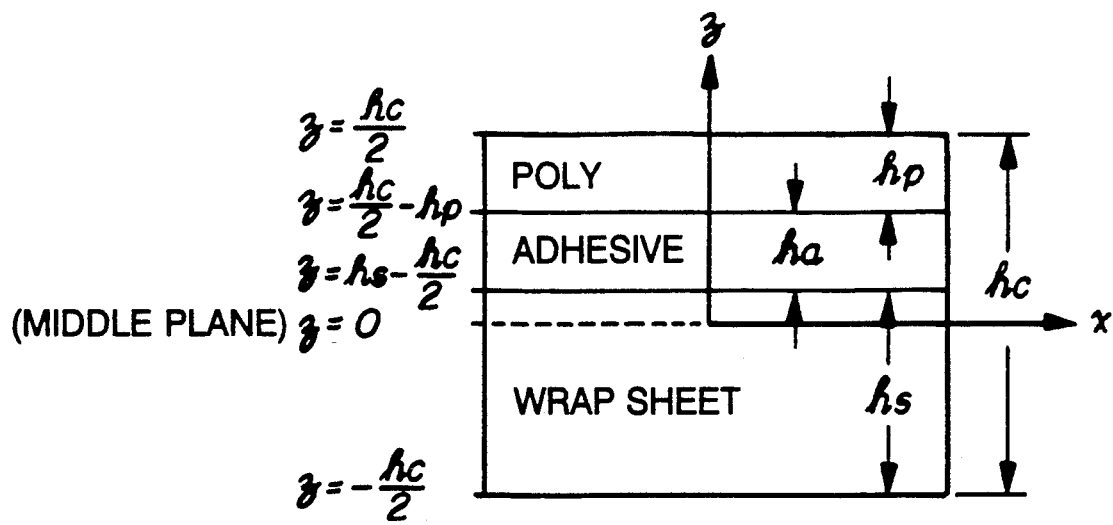
FIG. 7 representatively shows a schematic representation of a composite securing zone composed of an outer cover layer adhesively bonded to a second layer.

In the unbonded areas, the outer cover does not receive support from the wrap sheet. Consequently, the rigidity value of the securing zone in such unbonded areas is the rigidity value of the outer cover material by itself, which is given by $$R_p = E_p * w * h_p^3 / 12 \tag{4}$$

where:
$R_p$ = rigidity of the outer cover material
$E_p$ = Young's modulus of the outer cover material
$h_p$ = thickness of the outer cover material
w = 1 inch In the bonded area, the rigidity of the securing zone is substantially equivalent the rigidity value of a outer cover/adhesive/wrap sheet composite laminate. For such a 3-layer laminate, representatively shown in FIG. 7, the rigidity value is a sum of 3 parts, as described below:

$$R_c = (E_p * I_p) + (E_a * I_a) + (E_s * I_s) \tag{5}$$

where the subscripts "c", "p", "a", and "s" denote the properties for the composite laminate, outer cover material, adhesive, and wrap sheet, respectively.

The three moments of inertia $I_p$, $I_a$, and $I_s$, with respect to the middle plane of the laminate, are given by $$I_p = (w) * [(\tfrac{1}{2}*h_c)^3 - (\tfrac{1}{2}*h_c - h_p)^3]/3 \tag{6}$$

$$I_a = (w) * [(\tfrac{1}{2}*h_c - h_p)^3 - (h_s - \tfrac{1}{2}*h_c)^3]/3 \tag{7}$$

$$I_s = (w) * [(h_s - \tfrac{1}{2}*h_c)^3 - (-\tfrac{1}{2}*h_c)^3]/3 \tag{8}$$

Typically:

$$E_a << E_p, \text{ and } E_a << E_s. \tag{9}$$

As a result, the contribution from the adhesive can be neglected when calculating $R_c$ from equation (5). Accordingly, in the calculations for the following examples, $R_c$ is determined with the following equation:

$$R_c = (E_p * I_p) + (E_s * I_s) \tag{10}$$

where $I_p$ and $I_s$ are determined from equations (6) and (8), respectively.

Once the rigidity values in the bonded and unbonded areas are calculated from equations (4) and (10), the apparent or average rigidity, $R_o$, of the securing zone of the outer cover can be determined from the following equation (11).

$$R_o = ((100\% - \% \text{ bonded area}) * R_p) + ((\% \text{ bonded area}) * R_c) \tag{11}$$

The percent bonded area can be measured by conventional image analysis techniques, such as the technique set forth in the "Testing" section below, and represents the percentage of coverage by the construction adhesive on the inner surface of the outer cover over the area of the securing zone.

The rigidity ratio of a tape fastening system will be the ratio of the backing layer rigidity value ($R_b$) to the securing zone rigidity value ($R_o$); the ratio of equation (3) to equation (11).

In a particular aspect of the invention, the securing zone substrate comprises a two-layer laminate or other composite composed of outer cover 12 and a second layer of material, such as inner wrap sheet layer 56, which are at least partially bonded together by an open pattern of construction adhesive. Alternatively, the second layer of material may comprise a localized patch of fibrous or non-fibrous polymer material, which is bonded to either an inner or an outer major surface of the outer cover layer. In one embodiment, the securing zone is a composite comprising outer cover 12, and a layer of material adhered to an inner surface of the outer cover with an open pattern of adhesive which provides a multiplicity of secured and unsecured areas. The adhesive is arranged at the securing zone to provide an area coverage at least about 10% of the inner surface area of the outer cover, and the pattern of adhesive is composed of a plurality of linear or nonlinear lines of adhesive with a spacing between adjacent lines of not more than about 1 cm. Such adhesive lines may be continuous or discontinuous.

Figure 8:
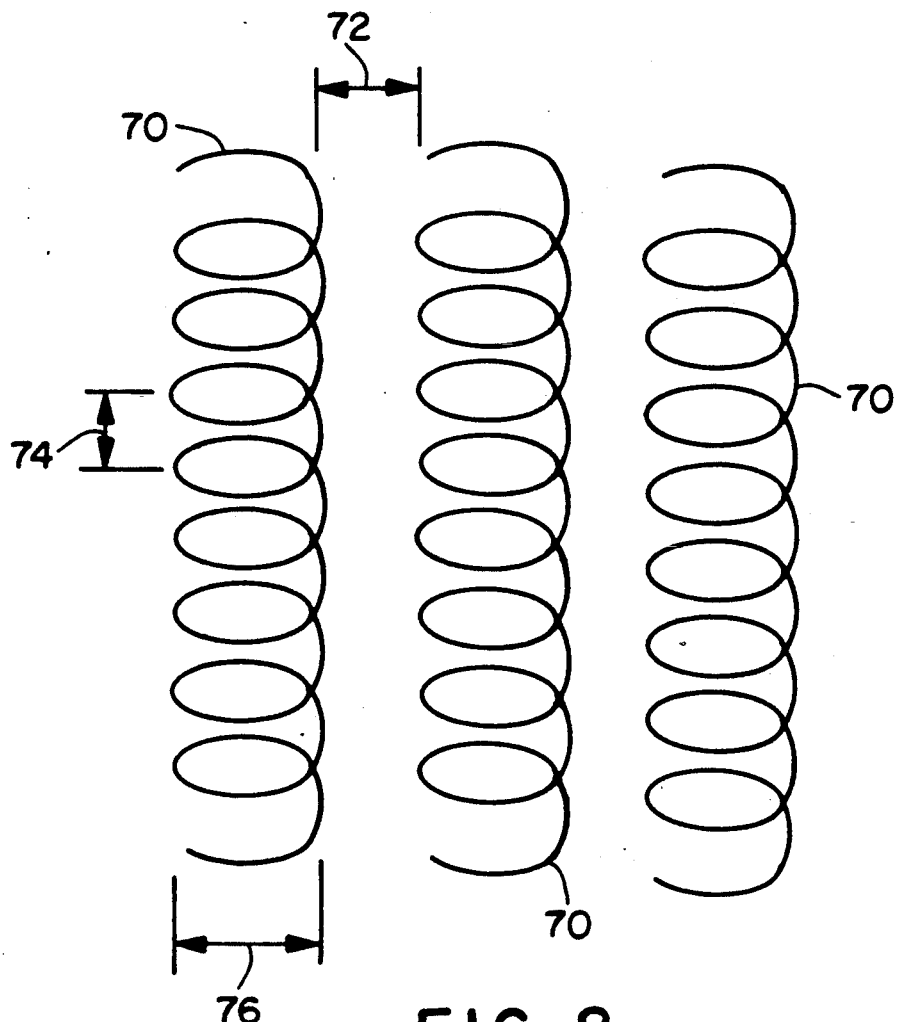
FIG. 8 representatively shows an open pattern of adhesive employed to form an embodiment of the invention wherein a composite securing zone comprises an outer cover layer and a second layer of material bonded to the outer cover with the adhesive pattern.

As representativlly shown in FIG. 8, for example, the open pattern of adhesive may comprise a plurality of swirled, looping arrays 70 which are located side-by-side with an array spacing 72 of not more than about 2 mm, and optionally, may overlap by a discrete distance In the illustrated embodiment, the arrays have a width 76 within the range of about 1.2–2.4 cm, and extend longitudinally along the length dimension of diaper 10. Within an array, the loop spacing 74 between successive swirls of adhesive along the length dimension of diaper 10 is not more than about 1 cm, preferably is within the range of about 0.2–1.0 cm, and more preferably is within the range of about 0.2–0.5 cm to provide improved effectiveness. In arrangements wherein the side-by-side arrays overlap by a discrete distance, the overlap distance is within the range of about 0.1 cm–0.9 cm, and preferably, the overlap distance is within the range of about 0.2–0.4 cm.

Certain aspects of the invention are configured with an adhesive add-on amount of not more than about 16 $gm/m^2$, preferably not more than about 12 $gm/m^2$, and more preferably not more than about 9 $gm/m^2$. In further aspects of the invention, the adhesive add-on amount is not less than about 2 $gm/m^2$, preferably is not less than about 4 $gm/m^2$, and more preferably is not less than about 6 $gm/m^2$. Suitable adhesives include, for example, National Starch NS 34-5541 and NS 34-5527 hot-melt adhesives available from National Starch and Chemical Company located in Bridgewater, N.J., and Findley H-4013 hot-melt adhesive available from Findley Adhesive Company located in Milwaukee, Wis. In the illustrated embodiment, the open pattern of adhesive comprises NS 34-5541 hot melt adhesive.

TESTING

Peak Tensile Strength

A suitable technique for determining the peak tensile strength of a material is a modified version of ASTM Standard Test Method D 882 (Test Method for Tensile Properties of Thin Plastic Sheeting). To measure peak strength for the purposes of the present invention, the following modifications are made to the standard procedure:

The rate of separation imparted to the grip members of the testing apparatus is kept at a rate of 50 mm/minutes for all samples.

The initial separation between the grip members is varied from 1 inch to 3 inches depending on the type of sample tested. The initial separation when testing tape backing materials is 1.5 inches, and the initial separation when testing outer cover materials and securement zone materials is 3 inches.

The peak strength is calculated by dividing the maximum load on the load-crosshead travel curve by the width of the sample.

180° Peel Adhesion Value

Figure 9:
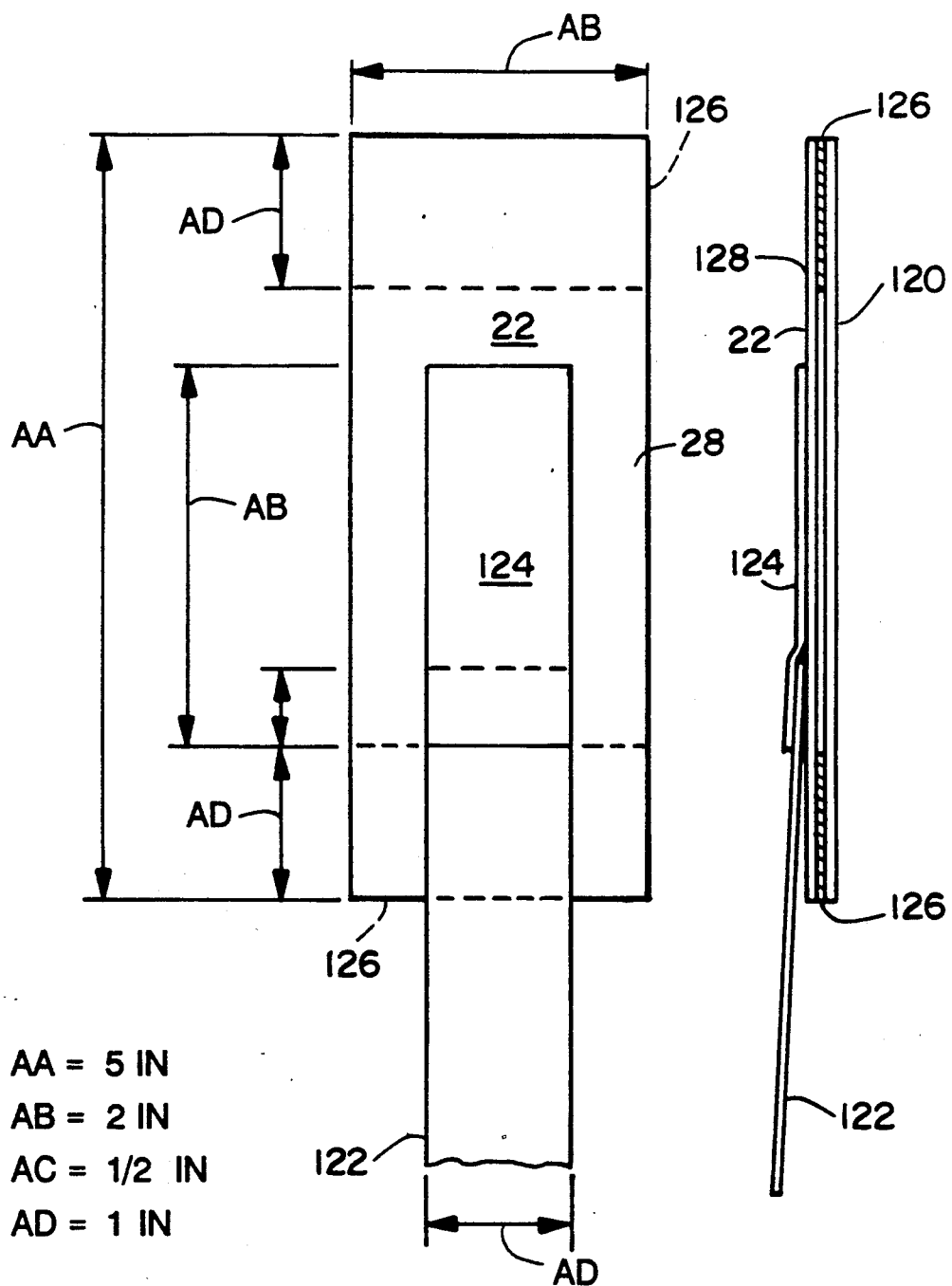
FIG. 9 representatively shows a top view of a test specimen for determining the peel adhesion value of an adhesive tab with respect to a selected securing zone surface.

A suitable technique for determining the 180° peel adhesion value between an adhesive tab and a selected landing surface can be determined by employing a modification of the Pressure-Sensitive Tape Council Test Procedure PSTC-4 (Adhesion to Liner of Pressure-Sensitive Tapes at 180° Angle). To determine the 180° peel adhesion value for the purposes of the present invention, the following modifications are made to the standard procedure:

With reference to FIGS. 9 and 9A, the test samples of the securing zone substrate material 128 are 2 inches wide and 5 inches long. The length dimension of the substrate sample generally corresponds with the direction along which the adhesive tab lies in the fastening system. For example, in a disposable diaper, the length dimension of substrate sample 128 typically lies along the cross-direction of the diaper article with which the substrate sample is intended for use. Double-sided adhesive tape 126 (1 inch wide) is applied to the top and bottom of the stainless steel test panel 120. Sufficient double-sided tape is employed to extend completely across the 2 inch wide steel test panel. The paper is removed from the double-sided tape and the test sample of substrate material 128 is adhered to the double-sided tape. Accordingly, the substrate material will be adhesively attached to the top and bottom regions of the steel test panel.

The test samples of adhesive tape tabs 124 are 1 inch wide and 2.5–3.0 inches long. The test sample of adhesive tab is adhered in overlapping relation with approximately ½ inch of one end of leading strip 122, which is composed of brown kraft wrapping paper measuring 1 inch wide by 9 inches long. The remaining 2–2.5 inches of tape tab 124 is adhered to the test area of the sample of securing zone substrate 128. The test area begins 1.5 inches from the end of the sample of substrate material, and the sample of adhesive tab is centered onto the substrate sample, leaving approximately ½ inch of exposed substrate material on both sides of the adhesive tab. The leading strip extends past the end of the substrate material. The test sample of adhesive tab is pressed down with a standard 4.5 lb. mechanical roller (available from Chemsultants International, a company having offices in Mentor, Ohio) by rolling the roller across the test tab once in each direction. The 180° peel adhesion test is then conducted immediately thereafter.

When placing the test specimen in the peel tester apparatus, the jaws of the peel tester are initially set 8 inches apart. One inch of the steel test panel is secured in the stationary jaw with the unsecured leading strip extending past the position of the stationary jaw. The leading strip is then doubled back and clamped in a centered arrangement within the moving jaw of the peel tester apparatus. The peel tester is then activated to conduct the 180° peel test wherein the sample of adhesive tab is effectively doubled back upon itself during the peeling operation.

The adhesive tab is peeled along a total distance of 65 mm. The first 10 mm of peel distance is ignored and the last 55 mm of peel distance is averaged and reported. The peel values are reported in grams per inch of tape tab width.

Cyclic Test Value

Figure 10:
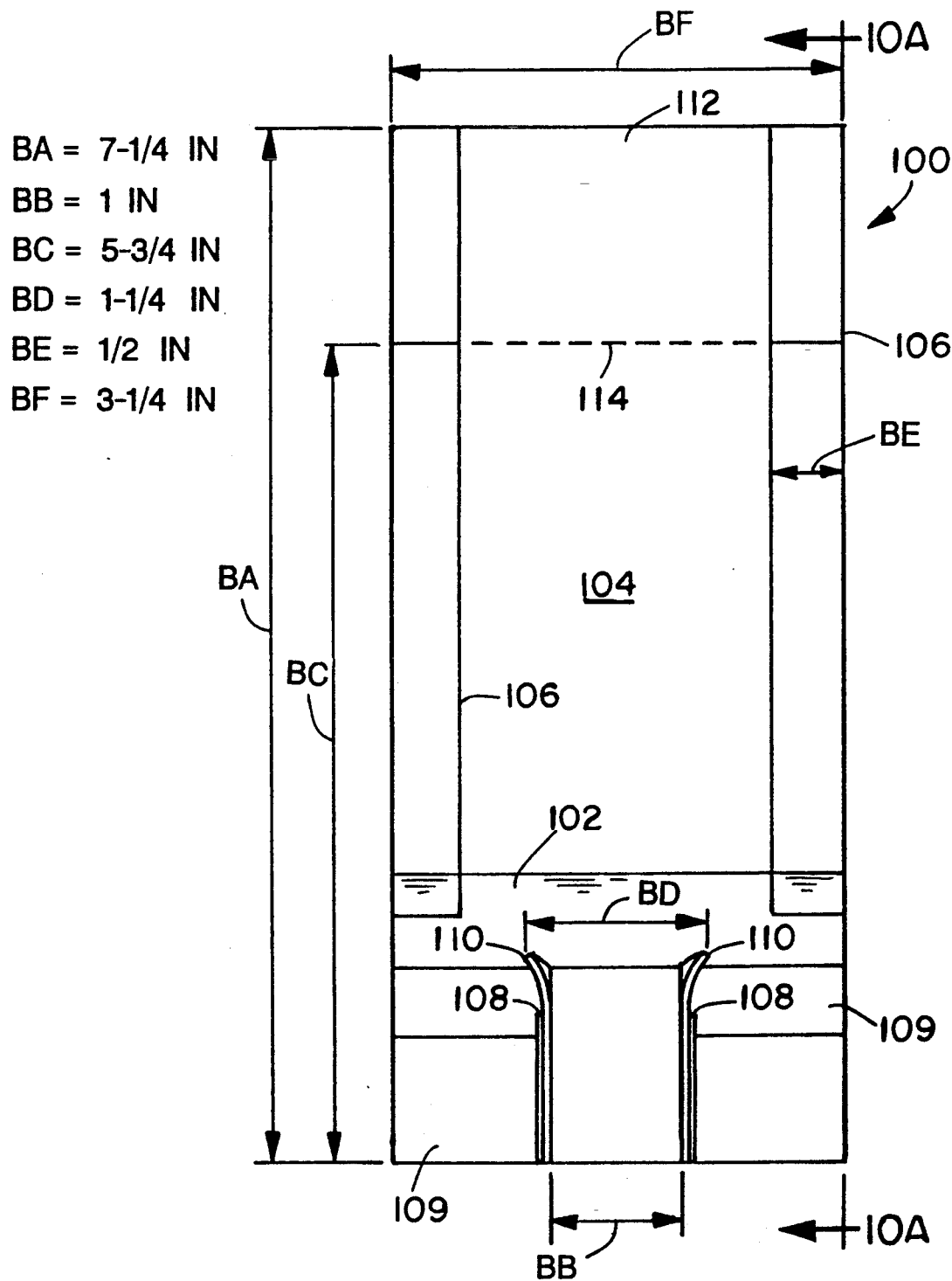
FIG. 10 representatively shows a front view of a testing fixture employed to determine a cyclic test value.
Figure 10A:
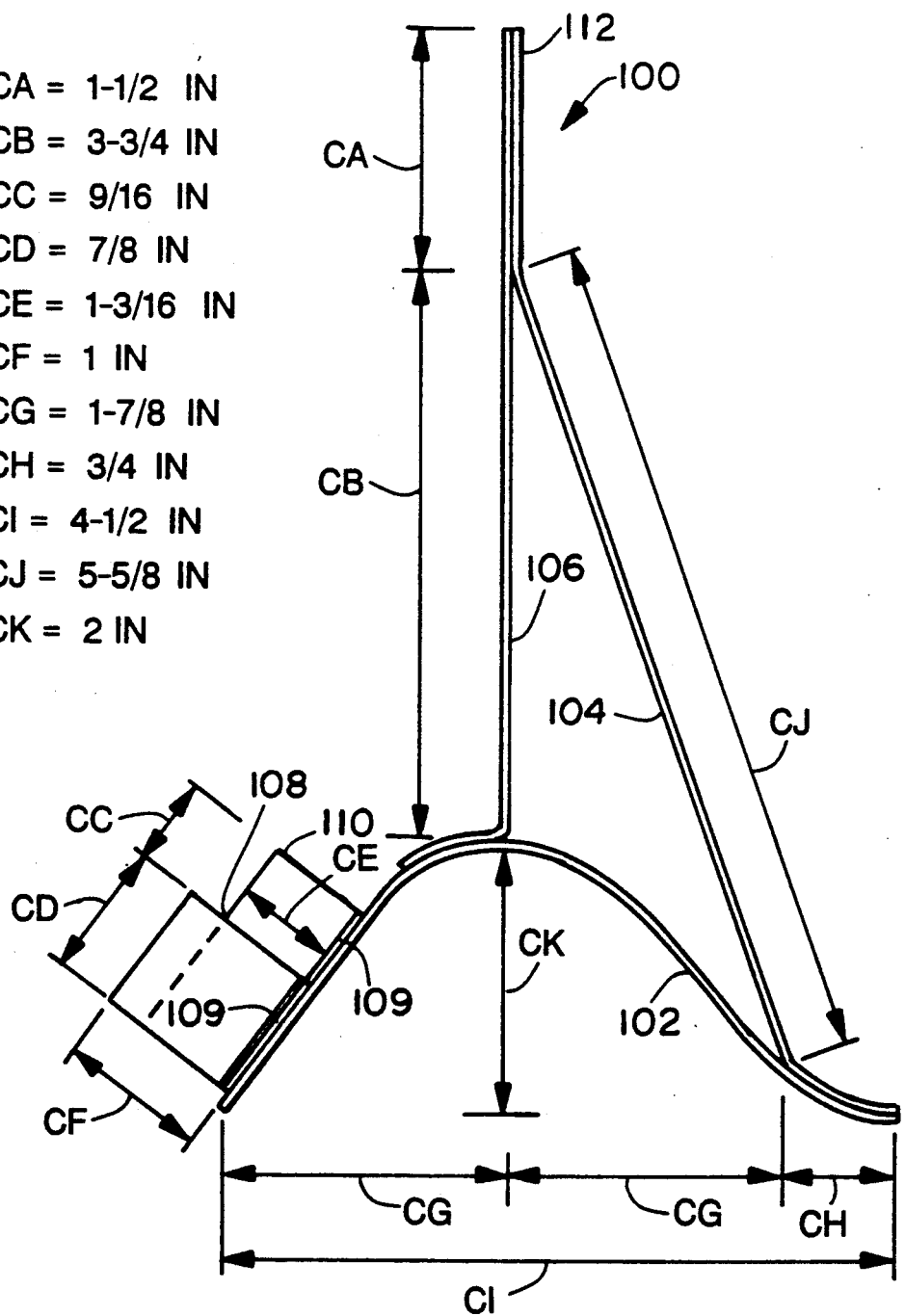
FIG. 10A representatively shows a side view of the testing fixture illustrated in FIG. 10.

To evaluate and test the security of the adhesive joint between the tape tab and the landing surface of the securement zone substrate, a cyclic test is employed to determine the number of stress cycles that an adhesive taping system can withstand without debonding. With regard to testing examples of the present invention, the cyclic test can be conducted in a configuration where the substrate is assembled to the underlying structure of its corresponding article. Such a test configuration can help approximate the environment of the taping system during actual use conditions. A suitable procedure for determining the Cyclic Test Value is a cyclic test employing the test fixture illustrated in FIGS. 10 and 10A. The dimensions of the test specimen are set forth in FIG. 11.

The test fixture can be constructed from aluminum sheet of the type commonly employed to make an exhaust duct for a household clothes dryer, and the measurements for the various parts of test fixture 100 are given in inches. The aluminum sheet is available from a retail consumer hardware store, and has a thickness of 0.016 inches. The aluminum sheet exhibited the following tensile properties, as obtained by ASTM Standard Test Method D 882:

Tensile Modulus: $3.65*10^5$ psi ($2.52*10^6$ kPa)
Yield Strength: $1.24*10^4$ psi ($8.55*10^4$ kPa)
Break Strength: $1.22*10^4$ psi ($8.41*10^4$ kPa)
Percent Strain at Yield: 8.41
Percent Strain at Break: 8.48

Cyclic Test Fixture 100 includes an arcuate, downwardly concave base member 102, a back member 104, two bracing arms 106, and two sample support members 108. The front section of base member 102 is relatively flat and has mounted thereon sample support members 108. The medial section of base member 102 is arcuate and curved concave down. The rear section of the base member may be generally planar or slightly reflexed to accommodate the connection and attachment of back member 104. The back member extends upwardly at an angle and is attached to a pair of bracing arms 106. The bracing arms are attached to the lateral side edges of back member 104 and extend downwardly to a region of attachment to the upwardly convex surface of the medial section of base member 102. The arcuate section of base member 102 has a radius of curvature of about 1.7 inch. In the illustrated embodiment, each sample support member 108 comprises two layers of sheet aluminum to provide increased stiffness. This configuration may be changed if the sample support members are constructed of a stiffer material, such as a thicker gauge of aluminum sheet. Sample support members 108 include mounting flanges 109 for attachment to base member 102. The rearmost corner 110 of each sample support member is outwardly flared by a distance of about ⅛ inch in a relatively smooth arc. The flared configuration facilitates the placement of the test sample between the sample support members.

The various parts of test fixture 100 are attached together with suitable fastening means, such as rivets, spot welds, high-strength adhesive or the like. The prototype test fixture, for example, was attached together by suitably wrapping the connecting regions of the component parts with conventional duct tape.

Figure 11:
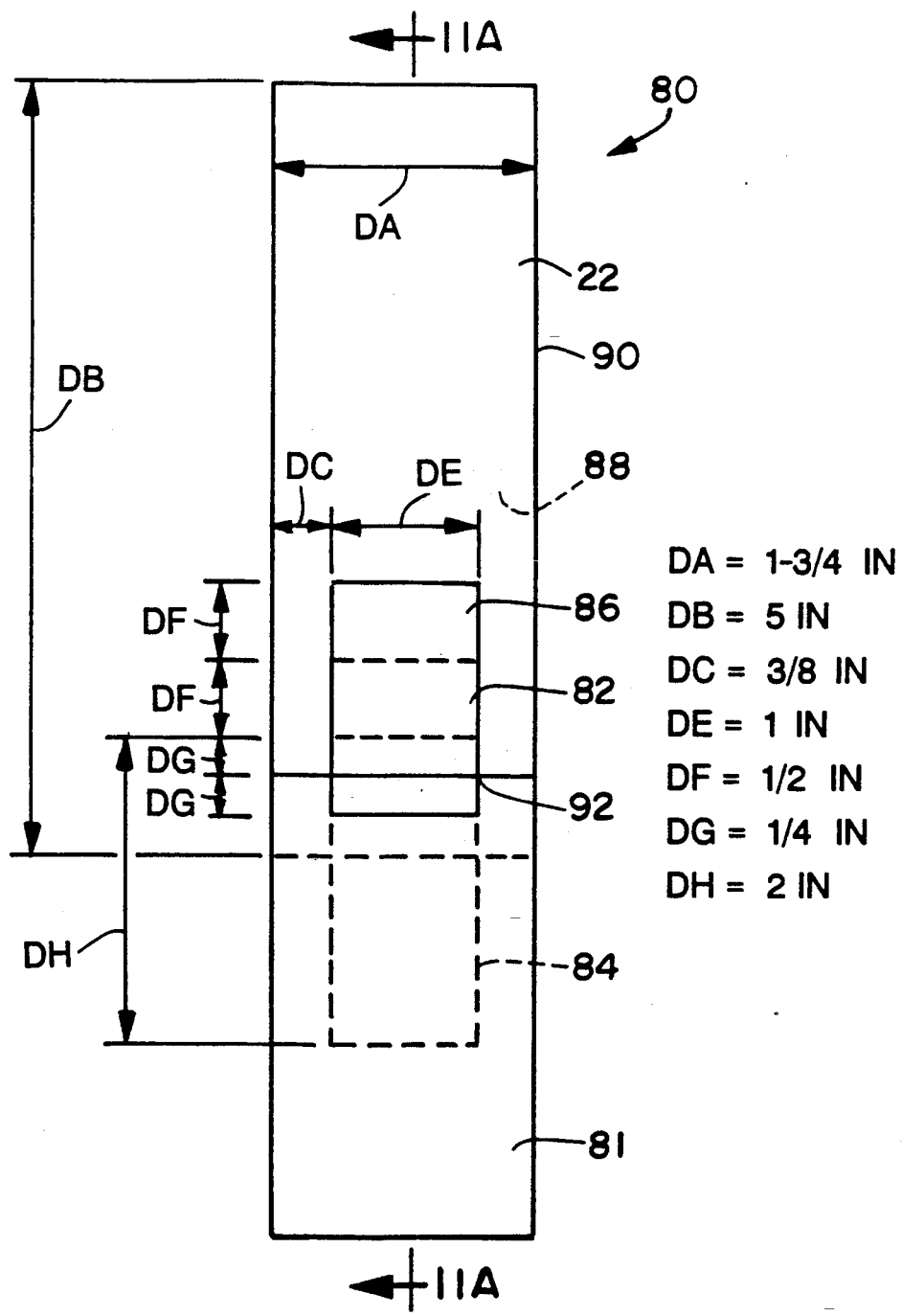
FIG. 11 representatively shows a top view of a test specimen for use in determining a cyclic test value.
Figure 11A:
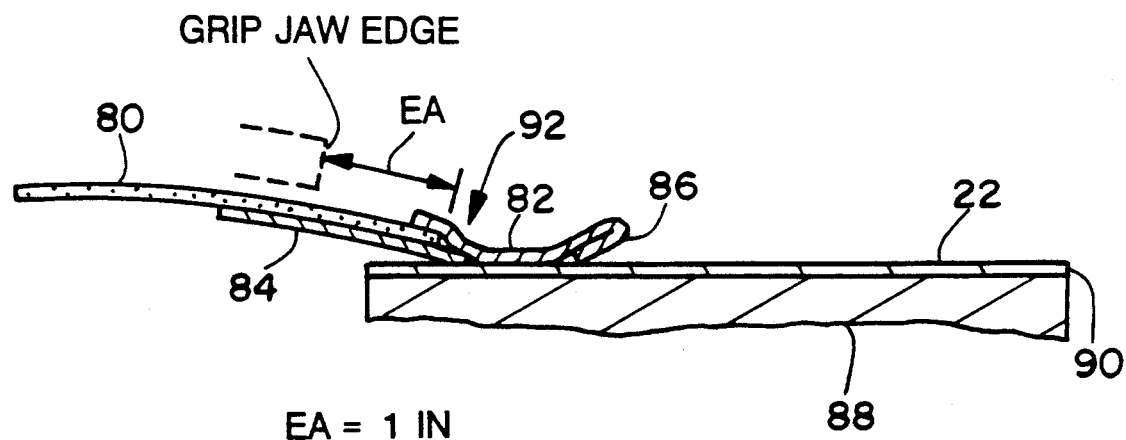
FIG. 11A representatively shows a side view of the test specimen of FIG. 11.

With reference to FIGS. 11 and 11A, test specimen 80 is composed of a test sample of adhesive tape tab 82 which is adhesively bonded to a test sample of securing zone substrate material 90. The substrate material is assembled to the underlying structure 88 of the article with which the substrate material is intended for use.

The test sample of the adhesive tape tab 82 is bonded to a leader strip 81 measuring 1.75 inches wide and at least 2.5 inches long. The material of a leader strip 81 should adhesively bond to tab sample 82 and anchor strip 84 with an adhesive bond strength which is stronger than the adhesive bond between tab sample 82 and substrate sample 90. In addition, the tensile load capacity of leader strip 81 should be greater than the adhesive bond between the tab sample and substrate sample, and should have a flexibility and stiffness which approximates the characteristics of the tape anchoring portion of the article with which the tape tab is intended for use. Leader strip 81 may, for example, be composed of a polymer material, such as a polyethylene strip, or a high-strength paper. In testing examples of the invention, leader strip 81 was composed of a 1 mil thick layer of polyethylene diaper outer cover material adhesively bonded and laminated to a layer of nonwoven fabric composed of spunbond polypropylene filaments forming a fabric basis weight of about 23.8 gsm (grams per sq. meter). The polyethylene film/spunbond laminate leader strip was cut from the sidewardly extending ear section of a commercial HUGGIES ® diaper. Tape sample 82 measures 1 inch wide and 2 inches long. A ¼ inch long end section is adhered to a terminal end of leader strip 81, and a ½ inch long section at the opposite end of the tab sample is doubled back and adhered against itself to form folded-over section 86.

A ¼ inch long, terminal end section of anchor strip 84 is adhered against the adhesive side of tab sample 82 and the remainder of the anchor strip is adhered to leader strip 81. Accordingly, tab sample 82 and anchor strip 84 are adhered to opposite sides of leader strip 81 with the leader strip sandwiched in a Y-bond 92. As a result, a remaining ½ inch long section of tab sample 82 is available for adhesive bonding to substrate sample 90. In the testing of the examples of the invention, the anchor end of tab sample 82 was adhered to the poly side of the leader strip and anchor strip 84 was adhered to the spunbond side of the leader strip.

Substrate sample 90 measures 1.75 inches wide and 5 inches long. The substrate sample is cut from the section of the article appointed for adhesion with the tape tab 82 intended for use with the adhesive fastening system. The substrate sample includes the outermost layer of the article, the innermost layer of the article, and the intermediate layers therebetween. The length of the substrate sample is aligned with the direction along which the adhesive tab lies in the fastening system. For example, in a disposable diaper, the length dimension of substrate sample 90 lies along the cross direction of the diaper article from which the substrate sample is taken. The edges of substrate sample 90 and suitably attached together to sufficiently maintain the integrity of the sample during cyclic testing. For the testing of the examples of the invention, the edges of the layers within the substrate sample were secured together with conventional ⅛ inch staples. The staples were positioned about ⅛ inch inward from the terminal edges of the sample, and were generally aligned end-to-end with about ⅜ inch between adjacent staples.

The bonding test area of tab sample 82 is ½ inch long and 1 inch wide, and is adhered to the landing surface 22 of the substrate sample in the center of the area extending between 0.75 inches and 1.25 inches from one end of the substrate sample. Folded-over section 86 of tab sample 82 faces toward the longer end of substrate sample 90, and leader strip 81 extends past the short end of the substrate sample. Tab sample 82 is pressed against the landing surface of substrate sample 90 with a standard, mechanically operated Roll-Down Machine· available from Chemsultants International located in Mentor, Ohio. The pressing roll should make a single pass on the tape and return.

The long end of substrate sample 90 is placed to extend between bracing arms 106 of cyclic test fixture 100 and extends one inch past bracing arms 106 and toward back member 104 of the cyclic test fixture. This end of substrate sample 90 is held in place against base member 102 with a suitable clamping mechanism located between back member 104 and bracing arms 106. The clamping mechanism exerts sufficient force to prevent shifting of the end of the substrate sample during cyclic testing. The clamping mechanism may, for example, be spring clips or an elastic rubber band wrapped over the top of the substrate sample and around underneath base member 102 of the cyclic test fixture. The remainder of substrate sample 90 and leader strip 81 extend over the arcuate hump of base member 102, and the specimen section wherein the substrate sample and tab sample are adhered together is pushed down between sample support members 108. Since the test specimen is somewhat wider than the space between support members 108, the specimen will forced to curve along the width dimension of the test specimen. The side-edge to side-edge curve of the test specimen should be concave up, with the concave surface facing away from base member 102 of the cyclic test fixture.

Figure 12:
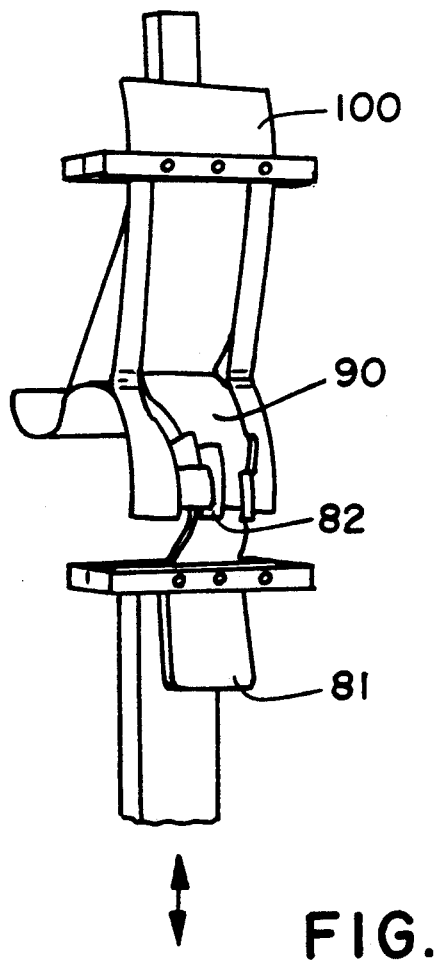
FIG. 12 representatively shows a perspective view of the assembled configuration of a testing fixture and sample which are arranged and connected to the testing machine employed for determining the cyclic test value.

As representatively shown in FIG. 12, the test fixture and test specimen are operably attached to a MTS Model No. 858 testing machine, which is available from MTS Company located in Minneapolis, Minn. The gripping jaws of the MTS testing machine are initially set 7 inches apart, and the top 1.75 inches section of back member 104 of the cyclic test fixture is clamped into the stationary, upper jaw. Leader strip 81 is clamped into the moveable lower law of the MTS machine, with the top edge of the moveable jaw positioned 1 inch from the end of the leader strip to which tab sample 82 is secured.

The cyclic test measures the number of cycles that the tape/securing substrate can sustain under cyclic motion before it completely detaches from the landing surface of the substrate. In this cyclic test, the frequency of the cyclic motion is kept at 1 Hz. To accelerate the debonding process, however, the span of the cyclic motion is initially set at 0.8 inch and increased every 300 cycles in the following sequence:

| Cycles | Span |
|---|---|
| 0–300 | 0.8 inch |
| 301–600 | 0.9 inch |
| 600–900 | 1.0 inch |
| 900–1200 | 1.05 inch |

(hereafter the span is increased by 0.05 inch for every 300 cycles)

Method for Determining Percent Area Coverage of Adhesive Patterns on a Substrate For the purposes of the present invention, the percent area coverage of the adhesive patterns applied onto a substrate can be determined by employing the following method. The adhesive material is stained or otherwise colored to contrast the adhesive from the remainder of the substrate material. For example, carbon black can be applied onto the adhesive patterns by rubbing the powdered carbon black with a hand or brush. The carbon black is removed from the non-adhesive areas by employing the hand or a soft brush to wash the substrate with a non-abrasive hand soap (e.g., Dial soap). The substrate is then dried by tamping with a paper towel. The samples are viewed with incident dark field illumination provided by a macro viewer, such as a Model MS36-MP4 "Mobil Studio" manufactured by Kreonite, Inc. located in Wichita, Kans., and four flood lamps, such as GE 100 watt flood lights. The flood lamps are regulated with an intensity control mechanism, such as a type 3PN1010 variable voltage autotransformer available from STACO Energy Products Co. located in Dayton, Ohio. The samples are viewed with a 50 mm EL-NIKKOR lens at f/4 to obtain a 2.25 by 1.75 inch field size. Three to five, and preferably ten fields are analyzed using a Quantimet 900 or 970 Image Analysis System, which is available from Leica/Cambridge, Inc. located in Deerfield, Ill. A suitable software routine for the analysis is the following "QUIPS" routine:

Enter Specimen Identity
Scanner (No. 1 Chalnicon LV=2.24 SENS=2.96 PAUSE)
Load Shading Corrector (pattern-BONDPA)
Calibrate User Specified (Cal value=1. picturepoint per pixel)
SUBRTN STANDARD
TOTPERCAR:=0
TOTFIELDS:=0
Print " "

For FIELD
Scanner (No. 1 Chalnicon LV=2.24 SENS=2.96 PAUSE)
Detect 2D (darker than 37. Delin PAUSE)
Pseudo-Colour Transfer - LUT COLOUR, full resolution, Text On,
Window (125,128)
Amend (OPEN by 1)
Live Frame is Rectangle (X:128, Y:101, W:640, H:529,)
Edit (pause)
Measure field - Parameters into Array FIELD
Print "PERCENT BOND AREA=", 100. * FIELD AREAFRACT
TOTPERCAR:=TOTPERCAR+100. * FIELD AREAFRACT
TOTFIELDS:=TOTFIELDS+1.
Pause
Next FIELD Print " "
Print "AVERAGE PERCENT BOND AREA=",
  TOTPERCAR/TOTFIELDS
END OF PROGRAM While the above software routine designates a Chalnicon scanner, it should be readily understood that another scanner, such as a Newvicon or Vidicon scanner, may optionally be employed, and the routine can be readily modified to address the selected scanner. The following examples are presented to provide a more detailed understanding of the invention. The particular materials and parameters are exemplary, and are not intended to specifically limit the scope of the invention.

EXAMPLES

Example 1

Figure 13:
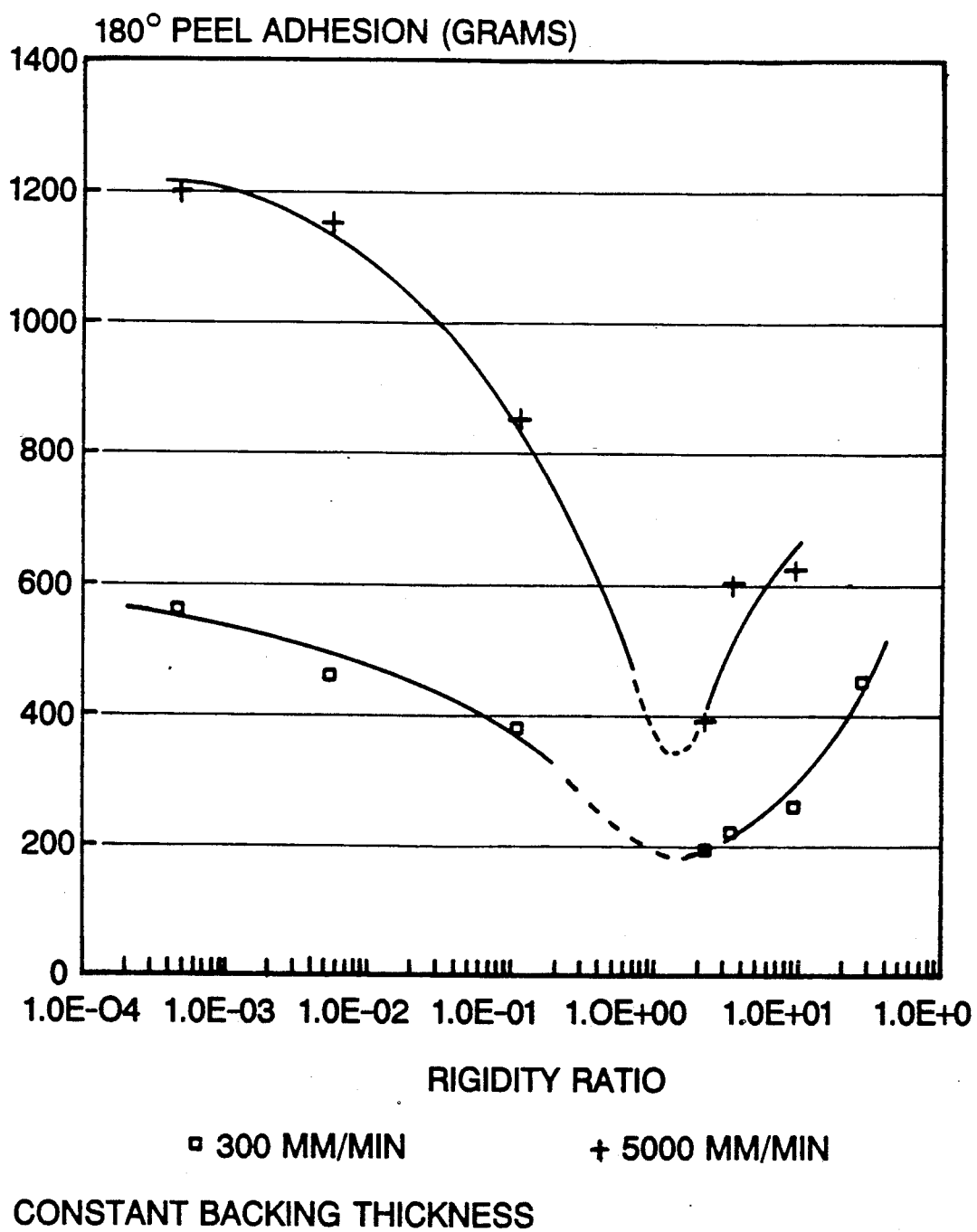
FIG. 13 schematically shows the change of peel adhesion value for different rigidity ratios where different materials are employed to reinforce a polyethylene film.

To confirm the effect of the rigidity ratio on the peel adhesion value, the change of peel adhesion value was investigated over a range of about six orders of magnitude of rigidity ratio, R, by employing different materials to reinforce polyethylene films. The results are summarized in FIG. 13. The adhesive tape tab was a one-inch wide Tesa 4120 tab wherein the tape backing layer was composed of polyvinyl chloride (PVC), and the adhesive layer was composed of a polyisoprene adhesive. For data point 7, the securing zone substrate was composed of a polyethylene film having a thickness of 1 mil ($2.54*10^{-3}$ cm). For data points 6 and 6', the securing zone substrate was composed of 1.5 mil ($3.81*10^{-3}$ cm) thick polyethylene film, and for data points 5 and 5', the substrate was composed of 2 mil ($5.08*10^{-3}$ cm) thick polyethylene film. The securing zone substrate for data points 4 and 4' was a composite composed of 1 mil ($2.54*10^{-3}$ cm) thick polyethylene film laminated to a 4.5 mil thick wrap sheet composed of a fibrous web of cellulosic tissue material. The adhesive used for the lamination was National Starch NS 34-5541 hot-melt adhesive, and the adhesive was arranged in a looping, swirl pattern, which provided a 14.1 percent bonded area between the polyethylene film and the wrap sheet. Data points 3 and 3' are for a composite, securing zone substrate composed of a laminate of 1 mil thick polyethylene, and one layer of polypropylene tape, Part No. Y-8452, manufactured by 3M Company, St. Paul, Minn. Data points 2 and 2' were generated with respect to a composite securing zone substrate composed of a 1 mil thick layer of polyethylene film and three layers of Part No. Y-8452 tape. Data points 1 and 1' were generated with respect to a composite substrate composed of a 1 mil thick polyethylene film laminated to seven layers of Part No. Y-8452 tape. Peel adhesion tests were run at two speeds, 300 mm/minute and 5000 mm/minute, and the resultant test data are plotted in the graph of FIG. 13.

Example 2

A preferred securing zone was composed of one layer of 1 mil thick polyethylene film and one 4.5 mil (0.011 cm) thick layer of wrap sheet composed of cellulose tissue. The film and wrap sheet were partially bonded by an open swirl pattern of National Starch 34-5541 hot melt construction adhesive. Details of the swirl pattern and of the adhesive add-on amounts are as follows: The open pattern of adhesive was composed of a plurality of swirl arrays. Each array had a cross-directional width within the range of about 1.4–1.8 cm, and extended longitudinally along the length dimension of the diaper. Within an individual array, the loop spacing between successive swirls of adhesive along the length dimension of the diaper was within the range of about 0.7–1.0 cm. The adhesive add-on amount was about 2.33 gm/m², and the adhesive coverage was approximately 14.1% of the area of the poly film in the securing zone.

To examine the role of the wrap sheet and construction adhesive, 180° peel tests were run on (a) the poly film alone, (b) the poly film with adhesive, and (c) the poly film with adhesive and wrap sheet. The adhesive tapes employed were Tesa No. 4120 tape manufactured by BDF Tesa Corporation, and a KR-3221 tape available from 3M Company. Peel tests were conducted on five samples of each type of tape, and the results of the peel tests are summarized in the following Table 1, wherein the listed numerical values represent an average of 5 sample test values:

TABLE 1

Effect of Wrap Sheet and Construction Adhesive on the Peel Adhesion Value (grams/inch)

| | Tesa Tape | | |
|---|---|---|---|
| Peel Rate | Polyethylene Film (PE) | PE/Adhesive | PE/Adhesive/ Wrap Sheet |
| 300 mm/min. | 450 gm/in | 260 gm/in | 193 gm/in |
| 5000 mm/min. | tear | tear | 392 |

| | KR-3221 Tape | | |
|---|---|---|---|
| Peel Rate | Polyethylene (PE) Film | PE Film/Adhesive | PE Film/ Adhesive/ Wrap Sheet |
| 300 mm/min. | tear | tear | 3 of 5 tear |
| 5000 mm/min. | tear | tear | 3 of 5 tear |

For the Tesa No. 4120 tape, at the peel rate of 300 mm/min, the peel adhesion value drops by nearly 40 percent, where the securing zone comprises a combination of polyethylene film and construction adhesive. By further bonding a layer of wrap sheet to the polyethylene film with the adhesive, the peel adhesion value drops by about 60 percent. It is believed that the reason for this reduction in peel adhesion value is that the presence of the construction adhesive render the polyethylene film more resistant to stretching or ripping. As a result, less energy is dissipated and less force is required to peel the tape away from the securing zone substrate. The structural role of the wrap sheet can be seen at the peel rate of 5000 mm/minute, where only the combination of polyethylene film adhesive and wrap sheet was not torn by the Tesa tape. For the KR-3221 tape which has a more aggressive adhesive, both the polyethylene alone and the polyethylene with adhesive were torn at both the low and high peel rates. With the help of the wrap sheet, however, only three of five polyethylene film/adhesive/wrap sheet securing zone substrates were ripped by the KR-3221 tape during the peel adhesion testing.

Example 3

A taping system included an adhesive fastening tape obtained from a LUVS-Girl disposable diaper purchased sometime between mid-August and mid-September 1990. The securing zone substrate was composed of polyethylene film adhesively bonded to a wrap sheet composed of cellulosic tissue material having a basis weight of about 20.8 g/m². Details of the taping system are as follows:
Tape
  Type: LUVS-Girl Adhesive: A-B-A block copolymer
Backing Layer Thickness: 6 mils (1.52*10$^{-2}$ cm)
Backing Layer Modulus: 5.63*10$^4$ psi (3.88*10$^5$ kPa)
Backing Rigidity: 1.01*10$^{-3}$ lb-in$^2$/(inch of width)
Securing Zone Substrate
  Type: Poly film adhered to wrap sheet layer obtained from a Huggies ® medium-size disposable diaper
  Polyethylene Film Thickness: 1 mil
  Polyethylene Film Modulus: 2.92*10$^4$ psi
  Polyethylene Peak Strength: 630 grams/(inch of width)
  Wrap Sheet Thickness: 4.5 mils
  Wrap Sheet Modulus: 3.6*10$^3$ psi
  Securing Substrate Thickness: 7 mils
  Rigidity in the Unbonded Area (Polyethylene Film Rigidity): 2.43*10$^{-6}$ lb-in$^2$/(inch width)
  Rigidity in the Bonded Area: 3.18*10$^{-4}$ lb-in$^2$/(inch width)
  Percent Bonded Area: 14.1 percent
  Securing Zone Substrate Rigidity: 4.7*10$^{-5}$ lb-in$^2$/(inch width)
Rigidity Ratio: 21.5
The polyethylene film provided the landing surface of the securing zone substrate. Under 180° Peel Tests, the securing zone substrates were torn at all three speeds (300, 1000, and 5000 mm/minute)

Example 4

In this Example, the taping system was similar to that of Example 3 and had the following characteristics:
Tape Tab
  Type: From LUVS-Girl diaper
  Adhesive: A-B-A Block Copolymer
  Backing Layer Thickness: 6 mils
  Backing Modulus: 5.63*10$^4$ psi
  Backing Rigidity: 1.01*10$^{-3}$ lb-in$^2$/(inch width)
Securing Zone Substrate
  Type: Poly film adhered to wrap sheet layer, obtained from a Drypers disposable diaper on a date between mid-August and mid-September 1990.
  Poly Thickness: 1.5 mil
  Poly Modulus: 2.91*10$^4$ psi
  Poly Peak Strength: 800 grams/(inch width)
  Wrap Sheet Thickness: 3.5 mils
  Wrap Sheet Modulus: 5.57*10$^3$ psi
  Substrate Thickness: 5.5 mils
  Rigidity in the unbonded area (Poly Rigidity): 8.18*10$^{-6}$ lb-in$^2$/(inch width)
  Rigidity in the bonded area: 2.22*10$^{-4}$ lb-in$^2$/(inch width)
  % Bonded Area: 41.7%
  Substrate Rigidity: 9.73*10$^{-5}$ lb-in$^2$/(inch width)
Rigidity Ratio: 10.4
Testing results were as follows:

| 180 Degree Peel Test Speed (mm/min) | Peel Adhesion (grams/inch) |
|---|---|
| 300 | 947 |
| 1000 | 548 |
| 5000 | 396 |

At each speed, the peel adhesion value was taken as an average of the results from five samples tested. It was observed that three and four outer covers showed significant deformation at 300 mm/min and 1000 mm/min, respectively. At the highest speed of 5000 mm/min, two outer covers were ripped.

To form the securing zone substrate, the poly outer cover and the wrap sheet were bonded by glue in a closely-spaced swirl patter which provided 41.7% bonded area. This high %-bonded area increased the reinforcement from the wrap sheet. As a result, the securing zone substrate had a higher rigidity value and the fastening system had a lower rigidity ratio than that of Example 3. The rigidity ratio, however, was still above the important rigidity ratio of 10. As a result, more than half of the outer covers tested exhibited either stretching or ripping. The deformation of the outer cover often initiated in the unbonded region where the rigidity value was nearly two orders of magnitude smaller than that in the bonded area.

Example 5

In this Example, the taping system was similar to that of Example 3 and had the following characteristics:
Tape Tab
  Type: KR-3221, obtained from Huggies ® diaper
  Adhesive: Kraton
  Backing Layer Thickness: 4 mils
  Backing Modulus: 7.74*10$^4$ psi
  Backing Rigidity: 4.13*10$^{-4}$ lb-in$^2$/(inch width)
Securing Zone Substrate
  Type: Poly film adhered to wrap sheet, obtained from Huggies ® diaper
  Poly Thickness: 1 mil
  Poly Modulus: 2.92*10$^4$ psi
  Poly Peak Strength: 630 grams/(inch width)
  Wrap Sheet Thickness: 4.5 mils
  Wrap Sheet Modulus: 3.60*10$^3$ psi
  Substrate Thickness: 7 mils
  Rigidity in the unbonded area (Poly Rigidity): 2.43*10$^{-6}$ lb-in$^2$/(inch width)
  Rigidity in the bonded area: 3.18*10$^{-4}$ lb-in$^2$/(inch width)
  Bonded Area: 14.1%
  Substrate Rigidity: 4.70*10$^{-5}$ lb-in$^2$/(inch width)
Rigidity Ratio: 8.8

| Test Results | |
|---|---|
| 180 Degree Peel Test Speed (mm/min) | Peel Adhesion (grams/inch) |
| 300 | 745 |
| 1000 | 562 |
| 5000 | 604 |

At each of the three speeds, three out of five securing zone substrates tested were either torn or stretched.
Cyclic Test: 2838 cycles
In this case, the KR-3221 tape was less rigid than the LUVS-type tape in the previous two Examples because of a thinner backing layer. Although the rigidity ratio of this system was slightly below 10, the poly still ripped or stretched on three out of five samples tested. Two factors may explain this result. First, the surface of the securing zone substrate appeared to be less smooth. The wrinkles in the unbonded region would not only have lower rigidity value but also could have induced higher stress concentration. The combination of these effects could have caused the poly to stretch if the tape happened to land on the wrinkles. The second factor was that the strength of the poly film was 630 grams/(inch width), which was low compared with the 800 grams/(inch width) exhibited by other poly films.

During the cyclic test performed on this system, the number of cycles to failure was found to be very high due to high peel adhesion value of the system.

Example 6

In this Example, the taping system was similar to that of Example 3 and had the following characteristics:
Tape Tab
  Type: KR-3221
  Adhesive: Kraton
  Backing Layer Thickness: 4 mils
  Backing Modulus: $7.74*10^4$ psi
  Backing Rigidity: $4.13*10^{-4}$ lb-in$^2$/(inch width)
Securing Zone Substrate
  Type Poly film bonded to wrapsheet, obtained from Drypers diaper
  Poly Thickness: 1.5 mils
  Poly Modulus: $2.91*10^4$ psi
  Poly Strength: 830 grams/(inch width)
  Wrap Sheet Thickness: 3.5 mils
  Wrap Sheet Modulus: $5.57*10^3$ psi
  Substrate Thickness.. 5.5 mils
  Rigidity in the unbonded area (Poly Rigidity): $8.18*10^{-6}$ lb-in$^2$/(inch width)
  Rigidity in the bonded area: $2.22*10^{-4}$ lb-in$^2$/(inch width)
  Bonded Area: 41.7%
  Substrate Rigidity: $9.73*10^{-5}$ lb-in$^2$/(inch width)
Rigidity Ratio: 4.2

| Test Results | |
| --- | --- |
| 180 Degree Peel Test Speed (mm/min) | Peel Adhesion (grams/inch) |
| 300 | 543 |
| 1000 | 427 |
| 5000 | 180 |

In this case, the rigidity ratio was smaller than that of Example 5 because of the more rigid securing zone substrate. As the rigidity ratio was significantly below the critical ratio of 10, no deforming of the poly was observed. The peel values were also lower than those in Example 5 due to the absence of poly stretching.

Example 7

In this Example, the taping system was similar to that of Example 3 and had the following characteristics:
Tape Tab
  Type: 3M Industrial Tape No. 483
  Adhesive: Rubber
  Backing Layer Thickness: 4 mils
  Backing Modulus: $1.82*10^4$ psi
  Backing Rigidity: $9.71*10^{-5}$ lb-in$^2$/(inch width)
Securing Zone Substrate
  Type: Poly film bonded to wrap sheet, obtained from Huggies® diaper
  Poly Thickness: 1 mil
  Poly Modulus: $2.92*10^4$ psi
  Poly Peak Strength: 630 grams/(inch width)
  Wrap Sheet Thickness: 4.5 mils
  Wrap Sheet Modulus: 3.60 E+03 psi
  Substrate Thickness: 7 mils
  Rigidity in the unbonded area (Poly Rigidity): $2.43*10^{-6}$ lb-in$^2$/(inch width)
  Rigidity in the bonded area: $3.18*10^{-4}$ lb-in$^2$/(inch width)
  % Bonded Area: 14.1%
  Outer Cover Rigidity $4.70*10^{-5}$ lb-in$^2$/(inch width)
Rigidity Ratio: 2.1

| Test Results | |
| --- | --- |
| 180 Degree Peel Test Speed (mm/min) | Peel Adhesion (grams/inch) |
| 300 | 103 |
| 1000 | 155 |
| 5000 | 282 |

Cyclic Test: 1543 cycles

This Example employed a 3M industrial tape No. 483 which had the lowest modulus among the three tapes studied. The rigidity ratio of this system was found to be well below 10. For such a low rigidity ratio, deformation of the outer cover was not observed, and relatively low peel values were obtained, as expected.

Despite the low peel adhesion, the number of cycles to failure was still over 1500 cycles. This was due to the low rigidity ratio which enabled the tape to conform to the diaper outer cover during the cyclic motion, and thus reduced the possibility of early pop-open.

Having thus described the invention in rather full detail, it will be readily apparent that various changes and modifications may be made without departing from the spirit of the invention. All of such changes and modifications are contemplated as being within the scope of the present invention, as defined by the following claims.

We claim:

1. An article, comprising:
  an outer cover having waistband sections positioned at opposite ends thereof and having an intermediate section which interconnects said waistband sections, said outer cover including a securing zone which is located at a first of said waistband sections and which provides a landing surface appointed for receiving adhesion of one or more adhesive tabs thereon, said securing zone having a peak strength of not more than about 2500 gm per inch of width and a selected rigidity value; and
  an adhesive tab located at least one lateral side edge of a second of said waistband sections for securing said waistband sections around a wearer, said tab including a backing layer and an adhesive layer, said tab having, when adhered to said landing surface, a 180 degree peel adhesion value which is not more than 600 gm per inch of width as measured at a peel speed of 300 mm/sec, said backing layer having a rigidity value selected to provide a rigidity ratio of not more than about 10:1, said rigidity ratio determined by dividing said backing layer rigidity value by said securing zone rigidity value, said securing zone and adhesive tab thereby providing a refastenable taping system.

2. An article as recited in claim 1, wherein at least one of said adhesive tab is located at each of said lateral side edges of said second of said waistband sections.

3. An article as recited in claim 1, wherein said rigidity ratio is not more than abut 7:1.

4. An article as recited in claim 1, wherein said rigidity ratio is not more than about 4:1.

5. An article as recited in claim 1, wherein said rigidity ratio is about 1:1.

6. An article as recited in claim 1, wherein said rigidity ratio is not less than about 1:10.

7. An article as recited in claim 1, wherein said rigidity ratio is not less than about 1:7.

8. An article as recited in claim 1, wherein said rigidity ratio is not less than about 1:4.

9. An article as recited in claim 1, further comprising: a topsheet layer positioned in facing relation with said outer cover; and an absorbent body interposed between said outer cover and topsheet layer.

10. An article as recited in claim 9, wherein said securing zone is a material having a rigidity value of not more than about $1*10^{-3}$ lb-in$^2$ per inch of width.

11. An article as recited in claim 9, wherein said tab backing layer has a rigidity value of not more than about $1*10^{-4}$ lb-in$^2$ per inch of width.

12. An article as recited in claim 9, wherein said adhesive tab and said securing zone are constructed to exhibit a cyclic test value of at least about 1000 cycles when said tab is adhered to said securing zone.

13. An article as recited in claim 9, wherein said securing zone is a composite having a plurality of layers.

14. An article as recited in claim 9, wherein said securing zone is a composite comprising:
said outer cover; and
a layer of material bonded to an outer surface of said outer cover.

15. An article as recited in claim 9, wherein said securing zone is a composite comprising:
said outer cover; and
a layer of polymer material bonded to an inner surface of said outer cover.

16. An article as recited in claim 9, wherein said securing zone is a composite comprising:
said outer cover; and
a layer of cellulosic material adhered to an inner surface of said outer cover with a swirl pattern of adhesive.

17. An article as recited in claim 9, wherein said securing zone is a composite comprising:
said outer cover; and
a layer of material adhered to an inner surface of said outer cover with a swirl pattern of adhesive, said adhesive applied at an add-on amount within the range of about 2-16 gm/m$^2$.

18. An article as recited in claim 9, wherein said securing zone is a composite comprising:
said outer cover; and
a layer of material adhered to an inner surface of said outer cover with a swirl pattern of adhesive, said adhesive applied at an add-on amount within the range of abut 2-16 gm/m$^2$, and said swirl pattern of adhesive composed of swirled, looping lines of adhesive with a longitudinal, length-dimension spacing between adjacent loop lines being not more than about 1 cm.

19. An article as recited in claim 9, wherein said securing zone is a composite comprising:
said outer cover; and
a layer of material adhered to an area of an inner surface of said outer cover at said securing zone, said layer adhered with an open pattern of adhesive which provides a multiplicity of bonded and unbonded areas, said adhesive arranged to cover at least about 10% of said inner surface area of said outer cover, said pattern of adhesive composed of a plurality of lines of adhesive with adjacent adhesive lines spaced apart by not more than about 1 cm.

20. An article as recited in claim 9, wherein said securing zone is a composite comprising:
said outer cover; and
a layer of material adhered to an inner surface of said outer cover with an open pattern of adhesive which provides a multiplicity of secured and unsecured areas, said adhesive arranged at said securing zone to cover at least about 10% of the inner surface of said outer cover, said pattern of adhesive composed of a plurality of swirled, looping lines of adhesive with a length-dimension spacing between adjacent loop lines of not more than about 1 cm.

21. An article as recited in claim 9, wherein said adhesive tab and securing zone provide a rigidity ratio of not less than about 1:10.

22. An article as recited in claim 9, wherein said adhesive tab and securing zone provide a rigidity ratio of not less than about 1:7.

23. An article as recited in claim 9, wherein said adhesive tab and securing zone provide a rigidity ratio of not less than about 1:4.

24. An article as recited in claim 21, wherein said securing zone provides a peak strength of not less than about 500 gm per inch of width.

25. An article as recited in claim 9, wherein said outer cover is composed of a material having a peak strength of not more than about 1500 gm per inch of width.

26. An article as recited in claim 25, wherein said outer cover is composed of a material having a peak strength of not less than about 500 gm per inch of width.

27. An article as recited in claim 9, wherein said tab backing is composed of a material having a Young's modulus of not more than about $2*10^4$ psi.

28. An article as recited in claim 27, wherein said tab backing is a sheet of a polymeric material.

29. An article as recited in claim 27, wherein said tab backing is composed of a material having a Young's modulus of not more than about $8*10^3$ psi.

30. An article, comprising:
an outer cover having waistband sections positioned at opposite ends thereof and having an intermediate section which interconnects said waistband sections, said outer cover including a securing zone which is located at a first of said waistband sections and which provides a landing surface appointed for receiving adhesion of one or more adhesive tabs thereon, said securing zone having a selected peak tensile strength and a rigidity value of not more than about $1*10^{-3}$ lb-in$^2$ per inch of width; and
an adhesive tab located at at least one lateral side edge of a second of said waistband sections for securing said waistband sections around a wearer, said tab including a backing layer and an adhesive layer, said tab having, when adhered to said landing surface, a 180 degree peel adhesion value which is not more than about 600 gm per inch of width as measured at a peel speed of 300 mm/sec, said tab backing layer having a rigidity value selected to provide a rigidity ratio of not more than about 10:1, said rigidity ratio determined by dividing said backing layer rigidity value by said securing zone rigidity value, said securing zone and adhesive tab thereby providing a refastenable taping system.

31. An article as recited in claim 30, wherein said 180 degree peel adhesion value is not more than about 67% of said peak strength of said securing zone.

32. An article as recited in claim 30, wherein said 180 degree peel adhesion value is not more than about 50% of said peak strength of said securing zone.

33. An article as recited in claim 30, wherein at least one of said adhesive tab is located at each of said lateral side edges of said second waistband section.

34. An article as recited in claim 30, wherein said securing zone has a peak strength of not more than about 2500 gm per inch of width.

35. An article as recited in claim 30, further comprising:
a topsheet layer positioned in facing relation with said outer cover; and
an absorbent body interposed between said outer cover and topsheet layer.

36. An article as recited in claim 30, wherein said tab backing layer has a rigidity value of not more than about $1*10^{-4}$ lb-in$^2$ per inch of width.

37. An article as recited in claim 30, wherein said adhesive tab and said securing zone are constructed to exhibit a cyclic test value of at least about 1000 cycles when said tab is adhered to said securing zone.

38. An article as recited in claim 30, wherein said securing zone is a composite having a plurality of layers.

39. An article as recited in claim 30, wherein said securing zone is a composite comprising:
said outer cover; and
a layer of material bonded to an outer surface of said outer cover.

40. An article as recited in claim 30, wherein said securing zone is a composite comprising:
said outer cover; and
a layer of polymer material bonded to an inner surface of said outer cover.

41. An article as recited in claim 30, wherein said securing zone is a composite comprising:
said outer cover; and
a layer of cellulosic material adhered to an inner surface of said outer cover with a swirl pattern of adhesive.

42. An article as recited in claim 30, wherein said securing zone is a composite comprising:
said outer cover; and
a layer of material adhered to an inner surface of said outer cover with a swirl pattern of adhesive, said adhesive applied at an add-on amount within the range of about 2-16 gm/m$^2$.

43. An article as recited in claim 30, wherein said securing zone is a composite comprising:
said outer cover; and
a layer of material adhered to an inner surface of said outer cover with a swirl pattern of adhesive, said adhesive applied at an add-on amount within the range of about 2-16 gm/m$^2$, and said swirl pattern of adhesive composed of swirled, looping lines of adhesive with a longitudinal, length-dimension spacing between adjacent loop lines being not more than about 1 cm.

44. An article as recited in claim 30, wherein said securing zone is a composite comprising:
said outer cover; and
a layer of material adhered to an area of an inner surface of said outer cover at said securing zone, said layer adhered with an open pattern of adhesive which provides a multiplicity of bonded and unbonded areas, said adhesive arranged to cover at least about 10% of said inner surface area of said outer cover, said pattern of adhesive composed of a plurality of lines of adhesive with adjacent adhesive lines spaced apart by not more than about 1 cm.

45. An article as recited in claim 30, wherein said securing zone is a composite comprising:
said outer cover; and
a layer of material adhered to an inner surface of said outer cover with an open pattern of adhesive which provides a multiplicity of secured and unsecured areas, said adhesive arranged at said securing zone to cover at least about 10% of the inner surface of said outer cover, said pattern of adhesive composed of a plurality of swirled, looping lines of adhesive with a length-dimension spacing between adjacent loop lines of not more than about 1 cm.

46. An article as recited in claim 30, wherein said adhesive tab and securing zone provide a rigidity ratio of not more than about 10:1.

47. An article as recited in claim 30, wherein said securing zone provides a peak strength of not more than about 2500 gm per inch of width.

48. An article as recited in claim 30, wherein said outer cover is composed of a material having a peak strength of not more than about 500 gm per inch of width.

49. An article as recited in claim 30, wherein said tab backing is composed of a material having a Young's modulus of not more than about $2*10^4$ psi.

50. An article as recited in claim 47, wherein said securing zone provides a peak strength of not less than about 500 gm per inch of width.

51. An article as recited in claim 48, wherein said outer cover is composed of a material having a peak strength of not less than about 500 gm per inch of width.

52. An article as recited in claim 49, wherein said tab backing is a sheet of a polymeric material.

53. An article as recited in claim 49, wherein said tab backing is composed of a material having a Young's modulus of not more than about $8*10^3$ psi.

54. An article, comprising:
an outer cover having waistband sections positioned at opposite ends thereof and having an intermediate section which interconnects said waistband sections, said outer cover including a securing zone which is located at a first of said waistband sections and which provides a landing surface appointed for receiving adhesion of one or more adhesive tabs thereon, said securing zone having a selected peak tensile strength and a rigidity value of not more than about $1*10^{-3}$ lb-in$^2$ per inch of width; and
an adhesive tab located at at least one lateral side edge of a second of said waistband sections for securing said waistband sections around a wearer, said tab including a backing layer and an adhesive layer, said tab having, when adhered to said landing surface, a 180 degree peel adhesion value which is less than the peak strength of said securing zone, said tab backing layer having a rigidity value selected to provide a rigidity ratio of not more than about 7:1, said rigidity ratio determined by dividing said backing layer rigidity value by said securing zone rigidity value, said securing zone and adhesive tab thereby providing a refastenable taping system.

55. An article, comprising:
an outer cover having waistband sections positioned at opposite ends thereof and having an intermediate section which interconnects said waistband sections, a topsheet layer positioned in facing relation with said outer cover, and an absorbent body interposed between said outer cover and topsheet layer, said outer cover including a securing zone which is located at a first of said waistband sections and which provides a landing surface appointed for receiving adhesion of one or more adhesive tabs thereon, said securing zone having a peak strength of not more than about 2500 gm per inch of width and a selected rigidity value; and an adhesive tab located at at least one lateral side edge of a second of said waistband sections for securing said waistband sections around a wearer, said tab including a backing layer and an adhesive layer, said tab having, when adhered to said landing surface a 180 degree peel adhesion value which is less than the peak strength of said securing zone, said backing layer having a rigidity value selected to provide a rigidity ratio of not more than about 7:1, said rigidity ratio determined by dividing said backing layer rigidity value by said securing zone rigidity value, said securing zone and adhesive tab thereby providing a refastenable taping system.

56. An article as recited in claim 55, wherein said securing zone is a material having a rigidity value of not more than about $1*10^{-3}$ lb-in$^2$ per inch of width.

57. An article as recited in claim 55, wherein said tab backing layer has a rigidity value of not more than about $1*10^{-4}$ lb-in$^2$ per inch of width.

58. An article as recited in claim 55, wherein said adhesive tab and said securing zone are constructed to exhibit a cyclic test value of at least about 1000 cycles when said tab is adhered to said securing zone.

59. An article as recited in claim 55, wherein said securing zone is a composite having a plurality of layers.

60. An article as recited in claim 55, wherein said securing zone is a composite comprising:
   said outer cover; and
   a layer of material bonded to an outer surface of said outer cover.

61. An article as recited in claim 55, wherein said securing zone is a composite comprising:
   said outer cover; and
   a layer of polymer material bonded to an inner surface of said outer cover.

62. An article as recited in claim 55, wherein said securing zone is a composite comprising:
   said outer cover; and
   a layer of cellulosic material adhered to an inner surface of said outer cover with a swirl pattern of adhesive.

63. An article as recited in claim 55, wherein said securing zone is a composite comprising:
   said outer cover; and
   a layer of material adhered to an inner surface of said outer cover with a swirl pattern of adhesive, said adhesive applied at an add-on amount within the range of abut 2-16 gm/m$^2$.

64. An article as recited in claim 55, wherein said securing zone is a composite comprising:
   said outer cover; and
   a layer of material adhered to an inner surface of said outer cover with a swirl pattern of adhesive, said adhesive applied at an add-on amount within the range of about 2-16 gm/m$^2$, and said swirl pattern of adhesive composed of swirled, looping lines of adhesive with a longitudinal, length-dimension spacing between adjacent loop lines being not more than about 1 cm.

65. An article as recited in claim 55, wherein said securing zone is a composite comprising:
   said outer cover; and
   a layer of material adhered to an area of an inner surface of said outer cover at said securing zone, said layer adhered with an open pattern of adhesive which provides a multiplicity of bonded and unbonded areas, said adhesive arranged to cover at least about 10% of said inner surface area of said outer cover, said pattern of adhesive composed of a plurality of lines of adhesive with adjacent adhesive lines spaced apart by not more than about 1 cm.

66. An article as recited in claim 55, wherein said securing zone is a composite comprising:
   said outer cover; and
   a layer of material adhered to an inner surface of said outer cover with an open pattern of adhesive which provides a multiplicity of secured and unsecured areas, said adhesive arranged at said securing zone to cover at least about 10% of the inner surface of said outer cover, said pattern of adhesive composed of a plurality of swirled, looping lines of adhesive with a length-dimension spacing between adjacent loop lines of not more than about 1 cm.

67. An article as recited in claim 55, wherein said adhesive tab and securing zone provide a rigidity ratio of not less than about 1:7.

68. An article as recited in claim 55, wherein said adhesive tab and securing zone provide a rigidity ratio of not less than about 1:4.

69. An article as recited in claim 55, wherein said outer cover is composed of a material having a peak strength of not more than about 1500 gm per inch of width.

70. An article as recited in claim 55, wherein said tab backing is composed of a material having a Young's modulus of not more than about $2*10^4$ psi.

* * * * *

UNITED STATES PATENT AND TRADEMARK OFFICE
CERTIFICATE OF CORRECTION

PATENT NO. : 5,147,347

DATED : September 15, 1992

INVENTOR(S) : Huang et al.

It is certified that error appears in the above-identified patent and that said Letters Patent is hereby corrected as shown below:

At column 1, line 45, delete "GB 2 129 89 A" and insert therefor -- GB 2 129 689 A --.

At column 15, line 31, after the word "distance", insert therefor --. --.

Signed and Sealed this

Second Day of November, 1993

*Attest:*

BRUCE LEHMAN

*Attesting Officer*   *Commissioner of Patents and Trademarks*